United States Patent [19]

Pellet et al.

[11] Patent Number: 4,751,340

[45] Date of Patent: Jun. 14, 1988

[54] SELECTIVE PRODUCTION OF PARA-AROMATICS

[75] Inventors: Regis J. Pellet, Croton-On-Hudson; Gary N. Long, Putnam Valley; Jule A. Rabo, Armonk, all of N.Y.

[73] Assignee: Union Carbide Corporation, Danbury, Conn.

[21] Appl. No.: 874,661

[22] Filed: Jun. 16, 1986

[51] Int. Cl.⁴ .................................................. C07C 2/68
[52] U.S. Cl. ................................................... 585/467
[58] Field of Search ........................................ 585/467

[56] References Cited

U.S. PATENT DOCUMENTS

| | | | |
|---|---|---|---|
| 3,716,597 | 2/1973 | Mitsche et al. | 585/467 |
| 3,894,090 | 7/1975 | Cleveland | 585/450 |
| 3,965,208 | 6/1976 | Butter et al. | 260/671 M |
| 4,029,716 | 6/1977 | Kaeding | 260/672 T |
| 4,034,053 | 7/1977 | Kaeding et al. | 260/672 T |
| 4,100,215 | 7/1978 | Chen | 260/671 M |
| 4,127,616 | 11/1978 | Rodewald | 260/671 R |
| 4,152,364 | 5/1979 | Chu | 585/454 |
| 4,250,345 | 2/1981 | Chu | 585/467 |
| 4,283,306 | 8/1981 | Herkes | 252/432 |
| 4,310,440 | 1/1982 | Wilson et al. | 585/467 |
| 4,440,871 | 4/1984 | Lok et al. | 585/467 |
| 4,500,651 | 2/1985 | Lok et al. | 502/164 |
| 4,554,143 | 11/1985 | Messine et al. | 585/482 |
| 4,567,029 | 1/1986 | Wilson et al. | 585/467 |

*Primary Examiner*—Curtis R. Davis
*Attorney, Agent, or Firm*—Gerald L. Coon

[57] ABSTRACT

Alkylation of aromatics is effected by use of an alkylating agent, e.g., methanol, and novel alkylation catalysts containing non-zeolitic molecular sieves.

19 Claims, No Drawings

SELECTIVE PRODUCTION OF PARA-AROMATICS

It is well known that the alkylation of aromatics may be carried out using aluminosilicate zeolites, e.g., the methylation of toluene to xylenes. Numerous U.S. patents have been issued on the use of a myriad of aluminosilicate zeolites as catalysts for the methylation of toluene. Representative of these patents include U.S. Pat. Nos. 3,965,208, 4,100,215, 4,127,616, 4,034,053. 4.029.716, 4,152.364 and 4,250,345. The scientific literature has also described alkylation processes as evidenced by Yashima et al., "Alkylation on Synthetic Zeolites", Journal of Catalysis, 16, 273 to 280 (1970).

What is not disclosed in the aforementioned prior art relating to the alkylation of aromatics is alkylation processes employing non-zeolitic molecular sieves. The use of a crystalline silica polymorph for the alkylation of aromatics is disclosed in U.S. Pat. No. 4,283,306.

SUMMARY OF THE INVENTION

The instant invention relates to the process for the selective para-alkylation of mono substituted aromatics, e.g., para- xylene production by reaction of toluene with a methylating agent, under effective methylation conditions. The instant process is carried out in the presence of a catalyst comprising at least one non-zeolitic molecular sieve characterized in its calcined form by an adsorption of isobutane of at least 2 percent by weight, preferably at least four percent by weight at a partial pressure of 500 torr and a temperature of 20° C. and are also characterized by an adsorption of triethylamine less than 5 percent (%) by weight, preferably less than 3 percent by weight, at a partial pressure of 2.6 torr and a temperature of 22° C. The specific non-zeolitic molecular sieves employed as alkylation catalysts in the instant process are discussed hereinafter.

DETAILED DESCRIPTION OF THE INVENTION

The instant invention relates to the alkylation of aromatic compounds and preferably to the preparation of xylene mixtures. The invention employs novel catalysts comprising at least one non zeolitic, microporous crystalline molecular sieve containing at least three framework elements as tetrahedral oxides and characterized in the calcined form by an adsorption of isobutane of at least 2 percent by weight, preferably at least 4 percent by weight at a partial pressure of 500 torr and a temperature of 20° C. and also characterized in the calcined form by an adsorption of triethylamine less than 5 percent (%) by weight, preferably less than 3 percent by weight, at a partial pressure of 2.6 torr and a temperature of 22° C. The non-zeolite molecular sieves employed herein are discussed hereinafter.

NON-ZEOLITIC MOLECULAR SIEVES ("NZMS")

The term "non-zeolitic molecular sieves" or "NZMS" is defined in the instant invention to include the "SAPO" molecular sieves of U.S. Pat. No. 4,440,871, "ELAPSO" molecular sieves as disclosed in U.S. Ser. No. 600,312, filed Apr. 13, 1984 and certain "MeAPO", "FeAPO", "TAPO" and "ELAPO" molecular sieves, as hereinafter described. Crystalline metal aluminophosphates (MeAPOs where "Me" is at least one of Mg, Mn, Co and Zn) are disclosed in U.S. Pat. No. 4,567,029, issued Jan. 28, 1986; crystalline ferroaluminophosphates (FeAPOs) are disclosed in U.S. Pat. No. 4,554,143, issued Nov. 19, 1985; titanium aluminophosphates (TAPOs) are disclosed in U.S. Pat. No. 4,500,651, issued Feb. 19, 1985; certain non-zeolitic molecular sieves ("ELAPO") are disclosed in EPC application No. 85104386.9 (publication No. 0158976, published Oct. 13, 1985 and No. 85104388.5 (publication No. 158349, published Oct. 16, 1985); and ELAPSO molecular sieves are disclosed in copending U.S. Ser. No. 600,312, filed Apr. 13, 1984 (EPC publication No. 0159624, published Oct. 30, 1985). The aforementioned applications and patents are incorporated herein by reference thereto. The nomenclature employed herein to refer to the members of the aforementioned NZMSs is consistent with that employed in the aforementioned applications or patents. A particular member of a class is generally referred to as a "-n" species wherein "n" is an integer, e.g., SAPO-11, MeAPO-11 and ELAPSO-31. In the following discussion on NZMSs set forth hereinafter the mole fraction of the NZMSs are defined as compositional values which are plotted in phase diagrams in each of the identified patents, published applications or copending applications.

ELAPSO MOLECULAR SIEVES

"ELAPSO" molecular sieves are described in copending U.S. Ser. No. 600,312, filed Apr. 13, 1984, (EPC publication No. 0159,624, published Oct. 30, 1985, incorporated herein by reference) as crystalline molecular sieves having three-dimensional microporous framework structures of $ELO_2$, $AlO_2$, $PO_2$, $SiO_2$ oxide units and having an empirical chemical composition on an anhydrous basis expressed by the formula:

$$mR: (EL_wAl_xP_ySi_z)O_2$$

wherein "R" represents at least one organic templating agent present in the intracrystalline pore system; "m" represents the molar amount of "R" present per mole of and $(EL_wAl_xP_ySi_z)O_2$ and has a value of from zero to about 0.3; "EL" represents at least one element capable of forming a three dimensional oxide framework, "EL" is characterized as an element having a mean "T-O" distance in tetrahedral oxide structures between about 1.51 Angstroms and about 2.06 Angstroms, "EL" has a cation electronegativity between about 125 kcal/g-atom to about 310 kcal/g-atom and "EL" is capable of forming stable M-O-P, M-O-Al or M-O-M bonds in crystalline three dimensional oxide structures having a "M-O" bond dissociation energy greater than about 59 kcal/g-atom at 298° K.; and "w", "x", "y" and "z" represent the mole fractions of "EL", aluminum, phosphorus and silicon, respectively, present as framework oxides said mole fractions being within the limiting compositional values or points as follows:

| Point | Mole Fraction | | |
| --- | --- | --- | --- |
| | x | y | (z + w) |
| A | 0.60 | 0.39–(0.01)p | 0.01(p + 1) |
| B | 0.39–(0.01p) | 0.60 | 0.01(p + 1) |
| C | 0.01 | 0.60 | 0.39 |
| D | 0.01 | 0.01 | 0.98 |
| E | 0.60 | 0.01 | 0.39 | where "p" is an integer corresponding to the number of elements "El" in the $(El_wAl_xP_ySi_z)O_2$ constituent.

The "ELAPSO" molecular sieves are also described as crystalline molecular sieves having three-dimensional microporous framework structures of $ELO_2$, $AlO_2$, $SiO_2$ and $PO_2$ tetrahedral oxide units and having an empirical chemical composition on an anhydrous basis expressed by the formula:

$$mR: (EL_wAl_xP_ySi_z)O_2$$

wherein "R" represents at least one organic templating agent present in the intracrystalline pore system; "m" represents the molar amount of "R" present per mole of $(EL_wAl_xP_ySi_z)O_2$ and has a value of from zero to about 0.3; "EL" represents at least one element capable of forming a framework tetrahedral oxide and is selected from the group consisting of arsenic, beryllium, boron, chromium, cobalt, gallium, germanium, iron, lithium, magnesium, manganese, titanium and zinc; and "w", "x", "y" and "z" represent the mole fractions of "EL", aluminum, phosphorus and silicon, respectively, present as tetrahedral oxides said mole fractions being within the limiting compositional values or points as follows:

| Point | Mole Fraction | | |
|---|---|---|---|
| | x | y | (z + w) |
| a | 0.60 | 0.39−(0.01)p | 0.01(p + 1) |
| b | 0.39−(0.01)p | 0.60 | 0.01(p + 1) |
| c | 0.10 | 0.55 | 0.35 |
| d | 0.55 | 0.10 | 0.35 | where "p" is as above defined.

The "ELAPSO" molecular sieves include numerous species which are intended herein to be within the scope of the term "non-zeolitic molecular sieves" such being disclosed in the following copending and commonly assigned applications, incorporated herein by reference thereto;

| U.S. Ser. No. | Filed | NZMS |
|---|---|---|
| 600,174 | April 13, 1984 | CoAPSO |
| 600,173 | April 13, 1984 | FeAPSO |
| 600,180 | April 13, 1984 | MgAPSO |
| 600,175 | April 13, 1984 | MnAPSO |
| 600,179 | April 13, 1984 | TiAPSO |
| 600,170 | April 13, 1984 | ZnAPSO |
| 600,168 | April 13, 1984 | CoMgAPSO |
| 600,182 | April 13, 1984 | CoMnMgAPSO |
| 845,984 | March 31, 1986 | AsAPSO |
| 845,255 | March 28, 1986 | BAPSO |
| 841,752 | March 20, 1986 | BeAPSO |
| 852,174 | April 15, 1986 | CAPSO |
| 845,985 | March 31, 1986 | GaAPSO |
| 852,175 | April 15, 1986 | GeAPSO |
| 847,227 | April 12, 1986 | LiAPSO |

TiAPSO MOLECULAR SIEVES

The TiAPSO molecular sieves of U.S. Ser. No. 600,179, filed Apr. 13, 1984 have three-dimensional microporous framework structures of $TiO_2$, $AlO_2$, $PO_2$ and $SiO_2$ tetrahedral oxide units having an empirical chemical composition on an anhydrous basis expressed by the formula:

$$mR: (Ti_wAl_xP_ySi_z)O_2$$

wherein "R" represents at least one organic templating agent present in the intracrystalline pore system; "m" represents the molar amount of "R" present per mole of $(Ti_wAl_xP_ySi_z)O_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a subclass of TiAPSO molecular sieves the values "w", "x", "y" and "z" in the above formula are within the tetragonal compositional area defined by points a, b, c and d, said points a, b, c and d representing the following values for "w", "x", "y" and "z":

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

TiAPSO compositions are generally synthesized by hydrothermal crystallization from a reaction mixture containing active resources of titanium, silicon, aluminum and phosphorus, and preferably an organic templating, i.e., structure-directing, agent, preferably a compound of an element or Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the TiAPSO product are obtained, usually a period of from hours to several weeks. Generally, the crystallization time is from about 2 hours to about 30 days and typically from about 4 hours to about 20 days. The product is recovered by any convenient method such as centrifugation or filtration.

In synthesizing the TiAPSO, it is preferred to employ a reaction mixture composition expressed in terms of the molar ratios as follows:

$$aR: (Ti_wAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 0.3; "b" has a value of from zero (0) to about 500, preferably between about 2 and about 300; and "w", "x", "y" and "z" represent the mole fractions of titanium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| | Mole Fraction | | |
|---|---|---|---|
| Point | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing titanium, aluminum, phosphorus and silicon as framework tetrahedral oxides are prepared as follows:

Preparative Reagents

TiAPSO compositions are typically prepared using numerous regents. Typical reagents which may be employed and abbreviations employed in U.S. Ser. No. 600,179 for such reagents are as follows:
  (a) Alipro: aluminum isopropoxide;
  (b) LUDOX-LS: LUDOX-LS is the tradename of DuPont for an aqueous solution of 30 weight percent $SiO_2$ and 0.1 weight percent $Na_2O$;
  (c) $H_3PO_4$: 85 weight percent aqueous phosphoric acid;
  (d) Tiipro: titanium isopropoxide;
  (e) TEAOH: 40 weight percent aqueous solution of tetraethylammonium hydroxide;
  (f) $Pr_2NH$: di-n-propylamine, $(C_3H_7)_2NH$;
  (g) $Pr_3NH$: tri-n-propylamine, $(C_3H_7)_3N$;
  (h) Quin: Quinuclidine, $(C_7H_{13}N)$;
  (i) MQuin: Methyl Quinuclidine hydroxide, $(C_7H_{13}NCH_3OH)$; and
  (j) C-hex: cyclohexylamine.

Preparative Procedures TiAPSOs may be prepared by forming a reaction mixture by adding the $H_3PO_4$ and the water. This mixture is mixed and to this mixture aluminum isopropoxide is added. This mixture is then blended until a homogeneous mixture is observed. To this mixture the LUDOX-LS is added and the resulting mixture blended (about 2 minutes) until a homogeneous mixture is observed.

The titanium isopropoxide is added to the above mixture and the resulting mixture blended until a homogeneous mixture is observed. The organic templating agent is then added to the resulting mixture and the resulting mixture blended until a homogeneous mixture is observed, i.e., about 2 to 4 minutes. When the organic templating agent is quinuclidine the procedure is modified such that the quinuclidine is dissolved in about one half the water and accordingly the $H_3PO_4$ is mixed with about one half the water. (The pH of the mixture is measured and adjusted for temperature). The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out at the autogenous pressure.

The products are removed from the reaction vessel and cooled.

MgAPSO MOLECULAR SIEVES

The MgAPSO molecular sieves of U.S. Ser. No. 600,180, filed Apr. 13, 1984 have three-dimensional microporous framework structures of $MgO_2^{-2}$, $AlO_2^{-}$, $PO_2^{+}$ and $SiO_2$ tetrahedral oxide units and have an empirical chemical composition on an anhydrous basis expressed by the formula:

mR: $(Mg_wAl_xP_ySi_z)O_2$ wherein "R" represents at least one organic templating agent present in the intracrystalline pore system; "m" represents the molar amount of "R" present per mole of $(Mg_wAl_xP_ySi_z)O_2$ and has a value from zero (0) to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the limiting compositional values or points as follows:

| | Mole Fraction | | |
|---|---|---|---|
| Point | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

In a preferred subclass of the MgAPSO molecular sieves the values "w", "x", "y" and "z" in the above formula are within the limiting compositional values or points as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MgAPSO compositions are generally synthesized by hydrothermal crystallization for an effective time at effective pressures and temperatures from a reaction mixture containing reactive sources of magnesium, silicon, aluminum and phosphorus, an organic templating, i.e., structure directing, agent, preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the MgAPSO product are obtained, usually a period of from several hours to several weeks. Generally, the crystallization period will be from about 2 hours to about 30 days with it typically being from about 4 hours to about 20 days for obtaining MgAPSO crystals. The product is recovered by any convenient method such as centrifugation or filtration.

In synthesizing the MgAPSO compositions, it is preferred to employ reaction mixture compositions expressed in terms of the molar ratios as follows:

aR: $(Mg_wAl_xP_ySi_z)O_2$: $bH_2O$ wherein "R" is an organic templating agent; "a" is the amount of organic templating agent "R" and can have a value within the range of from zero (0) to about 6 and is more preferably an effective amount greater than zero to about 6; "b" has a value of from zero (0) to about 500, preferably between about 2 and about 300; and "w", "x", "y" and "z" represent the mole fractions of magnesium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing magnesium, aluminum, phosphorus and silicon as framework tetrahedral oxides are prepared as follows:

Preparative Reagents

MgAPSO compositions are prepared using numerous reagents. Typical reagents which may be employed to prepare MgAPSOs include:
(a) Alipro: aluminum isopropoxide;
(b) CATAPAL: Trademark of Condea for hydrated pseudoboehmite;
(c) LUDOX LS: Trademark of DuPont for an aqueous solution of 30 weight percent $SiO_2$ and 0.1 weight percent $Na_2O$;
(d) $Mg(Ac)_2$: magnesium acetate tetrahydrate, $Mg(C_2H_3O_2):4H_2O$;
(e) $H_3PO_4$; 85 weight percent aqueous phosphoric acid in water;
(f) TBAOH: tetraethylammonium hydroxide (40 wt. % in water);
(g) $Pr_2NH$: di-n-propylamine;
(h) $Pr_3NH$: tri-n-propylamine;
(i) Quin: Quinuclidine;
(j) MQuin: Methyl Quinuclidine hydroxide, (17.9% in water);
(k) C-hex: cyclohexylamine;
(l) TEAOH: tetraethylammonium hydroxide (40 wt. % in water);
(m) DEEA: Diethylethanolamine;
(n) i-$Pr_2NH$: di-isopropylamine;
(o) TEABr: tetraethylammonium bromide; and
(p) TPAOH: tetrapropylammonium hydroxide (40 wt. % in water).

Preparative Procedures

The MgAPSO compositions may be prepared by preparing reaction mixtures having a molar composition expressed as:

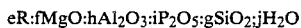

wherein e, f, g, h, i and j represent the moles of template R, magnesium (expressed as the oxide), $SiO_2$, $Al_2O_3$, $P_2O_5$ ($H_3PO_4$ expressed as $P_2O_5$) and $H_2O$, respectively.

The reaction mixtures may be prepared by the following representative procedures, designated hereinafter as Methods A, B and C.

Method A

The reaction mixture is prepared by mixing the ground aluminum source (Alipro or CATAPAL) with the $H_3PO_4$ and water on a gradual basis with occasional cooling with an ice bath. The resulting mixture is blended until a homogeneous mixture is observed. When the aluminum source is CATAPAL the water and $H_3PO_4$ is first mixed with the CATAPAL added thereto. The magnesium acetate is dissolved in portion of the water and is then added followed by addition of the LUDOX-LS. The combined mixture is blended until a homogenous mixture is observed. The organic templating agent is added to this mixture and blended until a homogenous mixture is observed. The resulting mixture (final reaction mixture) is placed in a lined (polytetrafluoroethylene) stainless steel pressure vessel and digested at a temperature (150° C. or 200° C.) for an effective time. Alternatively, if the digestion temperature is 100° C. the final reaction mixture is placed in a lined (polytetrafluoroethylene) screw top bottle for a time. Digestions are typically carried out at the autogenous pressure. The products are removed from the reaction vessel, cooled and evaluated as set forth hereinafter.

Method B

When method B is employed the organic templating agent is di-n-propylamine. The aluminum source, silicon source and one-half of the water are first mixed and blended until a homogeneous mixture is observed. A second solution was prepared by mixing the remaining water, the $H_3PO_4$ and the magnesium acetate. This solution is then added to the above mixture. The magnesium acetate and $H_3PO_4$ solution is then added to the above mixture and blended until a homogeneous mixture is observed. The organic templating agent(s) is then added and the resulting reaction mixture digested and product recovered as is done in Method A.

Method C

Method C is carried out by mixing aluminum isopropoxide, LUDOX LS and water in a blender or by mixing water and aluminum isopropoxide in a blender followed by addition of the LUDOX LS. $H_3PO_4$ and magnesium acetate are then added to this mixture. The organic templating agent is then added to the resulting mixture and digested and product recovered as is done in Method A.

MnAPSO MOLECULAR SIEVES

The MnAPSO molecular sieves of U.S. Ser. No. 600,175, filed Apr. 13, 1984 have a framework structure of $MnO_2^{-2}$, $AlO_2^-$, $PO_2^+$, and $SiO_2$ tetrahedral units having an empirical chemical composition on an anhydrous basis expressed by the formula:

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MnAPSO compositions are generally synthesized by hydrothermal crystallization from a reaction mixture containing reactive sources of manganese, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the MnAPSO product are obtained, usually a period of from several hours to several weeks. Typical effective times of from 2 hours to about 30 days with generally from about 4 hours to about 20 days have been observed. The product is recovered by any convenient method such as centrifugation or filtration.

In synthesizing the MnAPSO compositions, it is preferred to employ a reaction mixture composition expressed in terms of the molar ratios as follows:

aR: $(Mn_wAl_xP_ySi_z)O_2 : bH_2O$ 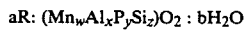

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of manganese, aluminum, phosphorus and silicon, respectively, and each has a value of at least 0.01.

In one embodiment the reaction mixture is selected such that the mole fractions "w", "x", "y" and "z" are generally defined as being within the compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing manganese, aluminum, phosphorus and silicon as framework tetrahedral oxide units are prepared as follows:

Preparative Reagents

MnAPSO compositions may be prepared by using numerous reagents. Reagents which may be employed to prepare MnAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) MnAc: Manganese acetate, $Mn(C_2H_3O_2)_2 \cdot 4H_2O$;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol.

Preparative Procedures

MnAPSOs are prepared by forming a starting reaction mixture by adding the $H_3PO_4$ to one half of the quantity of water. This mixture is mixed and to this mixture the aluminum isopropoxide or CATAPAL is added. This mixture is then blended until a homogeneous mixture is observed. To this mixture the LUDOX LS is added and the resulting mixture blended (about 2 minutes) until a homogeneous mixture is observed. A second mixture is prepared using the manganese acetate and the remainder (about 50%) of the water. The two mixtures are admixed and the resulting mixture blended until a homogeneous mixture is observed. The organic templating agent is then added to the resulting mixture and the resulting mixture blended until a homogeneous mixture is observed, i.e., about 2 to 4 minutes. (The pH of the mixture is measured and adjusted for temperature). The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out at the autogenous pressure.

CoAPSO MOLECULAR SIEVES

The CoAPSO molecular sieves of U.S. Ser. No. 600,174, filed Apr. 13, 1984 have three-dimensional microporous framework structures of $CoO_2^{-2}$, $AlO_2^-$, $PO_2^+$ and $SiO_2$ tetrahedral units and have an empirical chemical composition on an anhydrous basis expressed by the formula:

$$mR: (Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represent the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CoAPSO molecular sieves the values of "w", "x", "y", and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

CoAPSO compositions are generally synthesized by hydrothermal crystallization from a reaction mixture containing reactive sources of cobalt, silicon, aluminum and phosphorus, an organic templating, i.e., structure-directing, agent, preferably a compound of an element of Group VA of the Periodic Table, and optionally an alkali metal. The reaction mixture is generally placed in a sealed pressure vessel, preferably lined with an inert plastic material such as polytetrafluoroethylene and heated, preferably under autogenous pressure at an effective temperature which is generally between 50° C. and 250° C. and preferably between 100° C. and 200° C. until crystals of the CoAPSO product are obtained, usually for an effective time of from several hours to several weeks. Generally the effective crystallization time will be from about 2 hours to about 30 days and typically from about 4 hours to about 20 days. The product is recovered by any convenient method such as centrifugation or filtration.

In synthesizing the CoAPSO, it is preferred to employ a reaction mixture composition expressed in terms of the molar ratios as follows:

$$aR: (Co_wAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; and "w", "x", "y" and "z" represent the mole fractions of cobalt, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing cobalt, aluminum, phosphorus and silicon as framework tetrahedral oxide units are prepared as follows:

Preparative Reagents

CoAPSO compositions may be prepared using numerous reagents. Reagents which may be employed to prepared CoAPSOs include:
(a) Alipro: aluminum isoproproxide;
(b) CATAPAL: Trademark of Condea Corporation for pseudoboehmite;
(c) LUDOX-LS: Trademark of DuPont for an aqueous solution of 30 weight percent $SiO_2$ and 0.1 weight percent $Na_2O$;
(d) Co(Ac)$_2$: cobalt acetate $Co(C_2H_3O_2)_2*4H_2O$;
(e) $CoSO_4$: cobalt sulfate $(CoSO_4.7H_2O)$;
(f) $H_3PO_4$: 85 weight percent phosphoric acid in water;
(g) TBAOH: tetrabutylammonium hydroxide (25 wt. % in methanol);
(h) Pr$_2$NH: di-n-propylamine, $(C_3H_7)_2NH$;
(i) Pr$_3$N: tri-n-propylamine, $(C_3H_7)_3N$;
(j) Quin: Quinuclidine $(C_7H_{13}N)$;
(k) MQuin: Methyl Quinuclidine hydroxide, $(C_7H_{13}NCH_3OH)$;
(l) C-hex: cyclohexylamine;
(m) TEAOH: tetraethylammonium hydroxide (40 wt. % in water);
(n) DEEA: diethanolamine;
(o) TPAOH: tetrapropylammonium hydroxide (40 wt. % in water); and
(p) TMAOH: tetramethylammonium hydroxide (40 wt. % in water).

Preparative Procedure

CoAPSO compositions may be prepared by preparing reaction mixtures having a molar composition expressed as:

$$eR:f\ CoO:hAl_2O_3:iP_2O_5:gSiO_2:jH_2O$$

wherein e, f, h, i, g and j represent the moles of template R, cobalt (expressed as the oxide), $Al_2O_3$, $P_2O_5$($H_3PO_4$ expressed as $P_2O_5$), $SiO_2$ and $H_2O$, respectively.

The reaction mixtures are prepared by forming a starting reaction mixture comprising the $H_3PO_4$ and one half of the water. This mixture is stirred and the aluminum source (Alipro or CATAPAL) added. The resulting mixture is blended until a homogeneous mixture is observed. The LUDOX-LS is then added to the resulting mixture and the new mixture blended until a homogeneous mixture is observed. The cobalt source (e.g., Co(Ac)$_2$, Co(SO$_4$) or mixtures thereof) is dissolved in the remaining water and combined with the first mixture. The combined mixture is blended until a homogeneous mixture is observed. The organic templating agent is added to this mixture and blended for about two to four minutes until a homogeneous mixture is observed. The resulting mixture (final reaction mixture) is placed in a lined (polytetrafluoroethylene) stainless steel pressure vessel and digested at a temperature (150° C., 200° C. or 225° C.) for a time. Digestions are typically carried out at the autogenous pressure. The products are removed from the reaction vessel and cooled.

ZnAPSO MOLECULAR SIEVES

The ZnAPSO molecular sieves of U.S. Ser. No. 600,170, filed Apr. 13, 1984 comprise framework structures of $ZnO_2^{-2}$, $AlO_2^-$, $PO_2^+$ and $SiO_2$ tetrahedral units having an empirical chemical composition on an anhydrous basis expressed by the formula:

mR: $(Zn_wAl_xP_ySi_z)O_2$ wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of ZnAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

ZnAPSO compositions are generally synthesized by hydrothermal crystallization at effective process conditions from a reaction mixture containing active sources of zinc, silicon, aluminum and phosphorus, preferably an organic templating, i.e., structure directing, agent, preferably a compound of an element or Group VA of the Periodic Table, and/or optionally an alkali of other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the ZnAPSO product are obtained, usually a period of from several hours to several weeks. Generally the effective crystallization period is from about 2 hours to about 30 days with typical periods of from about 4 hours to about 20 days being employed to obtain ZnAPSO products. The product is recovered by any convenient method such as centrifugation or filtration.

In synthesizing the ZnAPSO compositions, it is preferred to employ a reaction mixture composition expressed in terms of the molar ratios as follows:

aR: $(Zn_wAl_xP_ySi_z)O_2$:b$H_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, more preferably between about 2 and about 300; and "w", "x", "y" and "z" represent the mole fractions of zinc, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing zinc, aluminum, phosphorus and silicon as framework tetrahedral oxide units are prepared as follows:

Preparative Reagents

ZnAPSO compositions are typically prepared numerous reagents. Reagents which may be employed to prepare ZnAPSOs include:

(a) Alipro: aluminum isopropoxide;

(b) LUDOX-LS: LUDOX-LS is the trade name of DuPont for an aqueous solution of 30 weight percent $SiO_2$ and 0.1 weight percent $Na_2O$;

(c) CATAPAL: Trademark of Condea Corporation for hydrated pseudoboehmite;

(d) $H_3PO_4$ : 85 weight percent aqueous phosphoric acid;

(e) ZnAc: Zinc Acetate, $Zn(C_2H_3O_2)_2.4H_2O$;

(f) TEAOH: 40% weight percent aqueous solution of tetraethylammonium hydroxide;

(g) TBAOH: 40 weight percent aqueous solution of tetrabutylammonium hydroxide;

(h) TMAOH: Tetramethylammonium hydroxide pentahydrate, $(CH_3)_4NOH.5H_2O$;

(i) TPAOH: 40 weight percent aqueous solution of tetrapropylammonium hydroxide, $(C_3H_7)_4$ NOH;

(j) Pr₂NH: di-n-propylamine, (C₃H₇)₂NH;
(k) Pr₃N: Tri-n-propylamine, (C₃H₇)₃N;
(l) Quin: Quinuclidine, (C₇H₁₃N);
(m) C-hex: cyclohexylamine; and
(n) DEEA: diethylethanolamine, (C₂H₅)₂NC₂H₅OH.

Preparative Procedure

ZnAPSO compositions are typically prepared by forming reaction mixtures having a molar composition expressed as:

eR:fZnO:gAl₂O₃:hP₂O₅:iSiO₂:jH₂O wherein e, f, g, h, i and j represent the moles of template R, zinc (expressed as the oxide), Al₂O₃, P₂O₅ (H₃PO₄ expressed as P₂O₅), SiO₂ and H₂O, respectively.

The reaction mixtures are generally prepared by forming a starting reaction mixture comprising the H₃PO₄ and a portion of the water. This mixture is stirred and the aluminum source added. The resulting mixture is blended until a homogeneous mixture is observed. The LUDOX LS is then added to the resulting mixture and the new mixture blended until a homogeneous mixture is observed. The zinc source (zinc acetate) is dissolved in the remaining water and combined with the first mixture. The combined mixture is blended until a homogenous mixture is observed. The organic templating agent is added to this mixture and blended for about two to four minutes until a homogenous mixture is observed. The resulting mixture (final reaction mixture) is placed in a lined (polytetrafluoroethylene) stainless steel pressure vessel and digested at an effective temperature for an effective time. Digestions are typically carried out at the autogenous pressure. The products are removed from the reaction vessel and cooled.

FeAPSO MOLECULAR SIEVES

The FeAPSO of U.S. Ser. No. 600,173, filed Apr. 13, 1984 have molecular sieves having a three dimensional microporous crystal framework structures of $FeO_2^{-2}$, (and or $FeO_2^-$), $AlO_2^-$, $PO_2^+$ and $SiO_2$ tetrahedral oxide units and having a unit empirical formula, on an anhydrous basis, of:

$$mR: (Fe_wAl_xP_ySi_z)O_2 \quad (1)$$

wherein "R" represents at least one organic templating agent present in the intracrystalline pore system; "m" represents the moles of "R" present per mole of $(Fe_wAl_xP_ySi_z)O_2$ and has a value of from zero (0) to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The FeAPSOs of the instant invention are generally synthesized by hydrothermal crystallization from a reaction mixture comprising reactive sources of iron, aluminum, phosphorus and silicon, and preferably one or more organic templating agents. Optionally, alkali or other metal(s) may be present in the reaction mixture and may act as templating agents. The reaction mixture is generally placed in a pressure vessel, preferably lined with an inert plastic material, such as polytetrafluoroethylene, and heated, preferably under the autogenous pressure, at an effective temperature which is generally between about 50° C., and about 250° C. and preferably between about 100° C. and 200° C. until crystals of the FeAPSO product are obtained, usually a period of from several hours to several weeks. Molecular sieves containing iron, aluminum phosphorus and silicon as framework tetrahedral oxide units are typically prepared as follows:

Preparative Reagents

FeAPSO compositions may be prepared using numerous reagents. Reagents which may employed to prepare FeAPSOs include:
(a) Alipro: aluminum isopropoxide, Al-(OCH(CH₃)₂)₃;
(b) LUDOX-LS: LUDOX-LS is the trademark of Du Pont for an aqueous solution of 30 weight percent SiO₂ and 0.1 weight percent Na₂O;
(c) CATAPAL: trademark for hydrated aluminum oxide containing about 75 wt. percent Al₂O₃ (pseudoboehmite phase) and about 25 wt. percent water;
(d) Fe(Ac)₂: Iron (II) acetate;
(e) FeSO₄: Iron (II) sulfate hexahydrate;
(f) H₃PO 4: 85 weight percent phosphoric acid in water;
(g) TEAOH: 40 weight percent aqueous solution of tetraethylammonium hydroxide;
(h) TBAOH: 40 weight percent aqueous solution of tetrabutylammonium hydroxide;
(i) Pr₂NH: di-n-propylamine ((C₃H₇)₂NH);
(j) Pr₃N: tri-n-propylamine ((C₃H₇)₃N);
(k) Quin: Quinuclidine (C₇H₁₃N);
(l) MQuin: Methyl Quinuclidine hydroxide (C₇H₁₃NCH₃OH);
(m) TMAOH: tetramethylammonium hydroxide pentahydrate; and
(o) C-hex: cyclohexylamine.

(a) Reaction mixtures to prepare FeAPSOs are typically prepared by grinding an aluminum isopropoxide in a blender followed by slowly adding a H₃PO₄ solution with mixing. A solution/ dispersion of iron acetate in water is added and then a silica (e.g., LUDOX-LS) is added. The organic templating agent is then added to this mixture, or in some cases one half of this mixture, and the mixture blended to form a homogeneous mixture. For example, in one embodiment, the number of moles of each component in the reaction mixture is as follows:

| Component | Moles |
|---|---|
| Al₂O₃ | 0.9 |
| P₂O₅ | 0.9 |
| SiO₂ | 0.2** |
| FeO* | 0.2 |
| TEAOH | 1.0 |
| H₂O | 50 |

*Iron (II) acetate reported as Iron (II) oxide.
**SiO₂ was 0.6 in examples 5C to 8C The reaction mixture is sealed in a stainless steel pressure vessel lined with polytetrafluoroethylene and heated in an oven at a temperature, time and at the autogenous pressure. The solid reaction product is recovered by filtration, washed with water and dried at room temperature.

In another embodiment, reaction mixtures are prepared by grinding the aluminum isopropoxide in a blender followed by addition of a solution/dispersion of iron (II) acetate. H₃PO₄ is added to this mixture and the resulting mixture blended to form a homogeneous mixture. A silica (e.g., LUDOX-LS) is added to this mixture except that in some instances the silica may be added with the H₃PO₄. The resulting mixtures were blended until a homogeneous mixture is observed. Organic templating agent is added to each mixture and the resulting mixtures placed in a stainless steel pressure vessel lined with polytetrafluoroethylene and heated, washed and the product recovered. In this embodiment the number of moles of each component in the reaction mixture is as follows:

| Component | Moles |
|---|---|
| Al₂O₃ | 0.9 |
| P₂O₅ | 0.9 |
| SiO₂ | 0.2 |
| FeO* | 0.2 |
| Template | 1.0 |
| H₂O | 50 |

*Iron (II) acetate reported as Iron (II) oxide.

CoMnAPSO MOLECULAR SIEVES

CoMnAPSO molecular sieves may be expressed by the empirical chemical formula (anhydrous) as follows:

mR: (Co$_u$Mn$_v$Al$_x$P$_y$Si$_z$)O$_2$ where "u", "v", "x", "y" and "z" represent the mole. The CoMnAPSO molecular sieves have an empirical chemical composition on an anhydrous basis expressed by the formula:

mR: (Co$_u$Mn$_v$Al$_x$P$_y$Si$_z$)O$_2$ wherein "R" represents at least one organic templating agent present in the intracrystalline pore system; "m" represents the molar amount of "R" present per mole of (Co$_u$Mn$_v$Al$_x$P$_y$Si$_z$)O$_2$ from zero (0) to about 0.3; an "u", "v", "x", "y" and "z" represent the mole fractions of cobalt, manganese, aluminum, phosphorus and silicon, respectively, present as tetrahedral oxides. The mole fractions "u", "v", "x", "y", and "z" are generally defined as being within the limiting compositional values or points as follows, wherein "w", the combined mole fractions of manganese and cobalt, is the sum of "u" and "v":

| Point | Mole Fraction | | |
|---|---|---|---|
| | x | y | (z + w) |
| A | 0.60 | 0.37 | 0.03 |
| B | 0.37 | 0.60 | 0.03 |
| C | 0.01 | 0.60 | 0.39 |
| D | 0.01 | 0.01 | 0.98 |
| E | 0.60 | 0.01 | 0.39 |

Preferably the mole fractions u, v, x, y and z will fall within the limiting compositional values or points as follows:

| Point | Mole Fraction | | |
|---|---|---|---|
| | x | y | (z + w) |
| a | 0.55 | 0.42 | 0.03 |
| b | 0.42 | 0.55 | 0.03 |
| c | 0.10 | 0.55 | 0.35 |
| d | 0.55 | 0.10 | 0.35 |

CoMnAPSO compositions are generally synthesized by hydrothermal crystallization from a reaction mixture containing reactive sources of cobalt, manganese, aluminum, phosphorus and silicon and preferably an organic templating agent, i.e., structure-directing, agent. The structure-directing agents are preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure and at typical effective temperatures between 50° C,. and 250° C., preferably between 100° C. and 200° C., until crystals of the CoMnAPSO product are obtained, usually over a period of from several hours to several weeks. Typical effective crystalliztion times are from about 2 hours to 30 days with from about 4 hours to about 20 days being generally empolyed to obtain CoMnAPSO products. The product is recovered by any convenient method such as centrifugaiton or filtration.

In synthesizing the CoMnAPSO compositions, it is preferred to empoly a reaction mixture composition expressed in terms of the molar ratios as follows:

aR:(Co$_u$Mn$_v$Al$_x$P$_y$Si$_z$)O$_2$:bH$_2$O wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "u", "v", "x", "y", and "z" represent the mole fractions of elements cobalt, manganese, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.37 | 0.03 |
| G | 0.37 | 0.60 | 0.03 |

-continued

| Point | Mole Fraction | | |
|---|---|---|---|
| | x | y | (z + w) |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "u", "v", "x", "y" and "z" such that $(u+v+x+y+z)=1.00$ mole. CoMnAPSO compositions were prepared using numerous regents.

Reagents which may be employed to prepare CoMnAPSOs include:
(a) Alipro: aluminum isopropoxide;
(b) LUDOX-LS: LUDOX-LS is the tradename of DuPont for an aqueous solution of 30 weight percent $SiO_2$ and 0.1 weight percent $Na_2O$;
(c) $H_3PO_4$: 85 weight percent phosphoric acid;
(d) MnAc: Manganese acetate, Mn $(C_2H_3O_2)_2 \cdot 4H_2O$;
(e) CoAc: Cobalt Acetate, Co $(C_2H_3O_2)_2 \cdot 4H_2O$;
(f) TEAOH: 40 weight percent aqueous solution of tetraethylammonium hydroxide; and
(g) $Pr_2NH$: di-n-propylamine, $(C_3H_7)_2NH$.

Preparative Procedures

CoMnAPSOs may be prepared by forming a starting reaction mixture by adding $H_3PO_4$ and one half of the quantity of water. To this mixture an aluminum isopropoxide is added. This mixture is then blended until a homogeneous mixture is observed. To this mixture a silica (e.g., LUDOX-LS) is added and the resulting mixture blended (about 2 minutes) until a homogeneous mixture is observed. A second mixture is prepared using manganese acetate and one half of the remaining water. A third mixture is prepared using cobalt acetate and one half of the remaining water. The three mixtures are admixed and the resulting mixture blended until a homogeneous mixture is observed. The organic templating agent is then added to the resulting mixture and the resulting mixture blended until a homogeneous mixture is observed, i.e., about 2 to 4 minutes. The pH of the mixture is measured and adjusted for temperature. The mixture is then placed in a lined (polytetrafluoroethylene) stainless steel pressure vessel and digested at a temperature Digestions are typically carried out at the autogenous pressure.

CoMnMgAPSO MOLECULAR SIEVES

The CoMnMgAPSO molecular sieves of U.S. Ser. No. 600,182, filed Apr. 13, 1984 have three-dimensional microporous framework structures of $CoO_2^{-2}$, $MnO_2^{-2}$, $MgO_2^{-2}$, $AlO_2^-$, $PO_2^+$ and $SiO_2$ tetrahedral oxide units and have an empirical chemical composition on an anhydrous basis expressed by the formula:

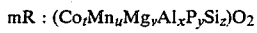

wherein "R" represents at least one organic templating agent present in the intracrystalline pore system; "m" represents the molar amount of "R" present per mole of $(Co_tMn_uMg_vAl_xP_ySi_z)O_2$, and has a value of from zero to about 0.3; and "t", "u", "v", "x", "y" and "z" represent the mole fractions of cobalt, manganese, magnesium, aluminum, phosphorus and silicon, respectively, present as tetrahedral oxides, each having a value of at least 0.01. The mole fractions "t", "u", "v", "x", "y" and "z" are generally defined as being within the limiting compositional values or points as follows, wherein "w", the combined mole fractions of cobalt, manganese and magnesium, is the sum of "t", "u" and "v":

| Point | Mole Fraction | | |
|---|---|---|---|
| | x | y | (z + w) |
| A | 0.60 | 0.36 | 0.04 |
| B | 0.36 | 0.60 | 0.04 |
| C | 0.01 | 0.60 | 0.39 |
| D | 0.01 | 0.01 | 0.98 |
| E | 0.60 | 0.01 | 0.39 |

In a preferred subclass of the CoMnMgAPSO molecular sieves the values of "w", "x", "y" and "z" in the above formula are within the limiting compositional values or points as follows:

| Point | Mole Fraction | | |
|---|---|---|---|
| | x | y | (z + w) |
| a | 0.55 | 0.41 | 0.04 |
| b | 0.41 | 0.55 | 0.04 |
| c | 0.10 | 0.55 | 0.35 |
| d | 0.55 | 0.10 | 0.35 |

CoMnMgAPSO compositions are generally synthesized by hydrothermal crystallization from a reaction mixture containing reactive sources of cobalt, manganese, magnesium, aluminum, phosphorus and silicon, and preferably an organic templating agent, i.e., structure-directing, agent. The structure-directing agents are preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° until crystals of the CoMnMgAPSO product are obtained, usually over a period of from several hours to several weeks. Typical crystallization times are from about 2 hours to about 30 days with from about 4 hours to about 20 days generally being employed to obtain CoMnMgAPSO products. The product is recovered by any convenient method such as centrifugation or filtration.

In synthesizing the CoMnMgAPSO compositions, it is preferred to employ a reaction mixture composition expressed in terms of the molar ratios as follows:

wherein "R" is an organic templating agent; "a" is the amount of organic templating agent "R" and has a value of from zero to about 6 and is preferably an effective amount within the range of greater than zero (0) to about 6 and more preferably from greater than zero to about 2; "b" has a value of from zero (0) to about 500, preferably between about 2 and about 300; and "t", "u", "v", "x", "y", and "z" represent the mole fractions of cobalt, manganese, magnesium, aluminum, phosphorus and silicon, respectively, and each has a value of at least 0.01.

In a preferred embodiment the reaction mixture is selected such that the mole fractions "w", "x", "y" and "z" where "w" is the sum of "t"+"u"+"v" are generally defined as being within the limiting compositional values or points as follows:

| Point | Mole Fraction | | |
|---|---|---|---|
| | x | y | (z + w) |
| F | 0.60 | 0.36 | 0.04 |
| G | 0.36 | 0.60 | 0.04 |
| H | 0.01 | 0.60 | 0.39 |
| I | 0.01 | 0.01 | 0.98 |
| J | 0.60 | 0.01 | 0.39 |

| Point | Mole Fraction | | |
|---|---|---|---|
| | x | y | (z + w) |
| F | 0.60 | 0.36 | 0.04 |
| G | 0.36 | 0.60 | 0.04 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "t", "u", "v", "x", "y" and "z" such that $(t+u+v+x+y+z) = 1.00$ mole. Molecular sieves containing cobalt, manganese, aluminum, phosphorus and silicon as framework tetrahedral oxide units are prepared as follows:

Preparative Reagents

CoMnMgAPSO compositions may be prepared by using numerous reagents. Reagents which may be employed to prepare CoMnAPSOs include:

(a) Alipro: aluminum isopropoxide;
(b) LUDOX-LS: LUDOX-LS is the tradename of Du Pont for an aqueous solution of 30 weight percent SiO$_2$ and 0.1 weight percent Na$_2$O;
(c) H$_3$PO$_4$: aqueous solution which is 85 weight percent phosphoric acid;
(d) MnAc: Manganese acetate, Mn(C$_2$H$_3$O$_2$)$_2$·4H$_2$O;
(e) CoAc: Cobalt Acetate, Co(C$_2$H$_3$O$_2$)$_2$·4H$_2$O;
(f) MgAc: Magnesium Acetate Mg(C$_2$H$_3$O$_2$)$_2$·4H$_2$O;
(g) TEAOH: 40 weight percent aqueous solution of tetraethylammonium hydroxide; and
(h) Pr$_2$NH: di-n-propylamine, (C$_3$H$_7$)$_2$NH.

Preparative Procedures

CoMnMgAPSOs may be prepared by forming a starting reaction mixture by adding H$_3$PO$_4$ and one half of the quantity of water. To this mixture an aluminum isoproxide is added. This mixture is then blended until a homogeneous mixture is observed. To this mixture a silica (e.g., LUDOX-LS) is added and the resulting mixture blended (about 2 minutes) until a homogeneous mixture is observed.

Three additional mixtures are prepared using cobalt acetate, magnesium acetate and manganese acetate using one third of the remainder of the water for each mixture. The four mixtures are then admixed and the resulting mixture blended until a homogeneous mixture is observed. An organic templating agent is then added to the resulting mixture and the resulting mixture blended until a homogeneous mixture is observed, i.e., about 2 to 4 minutes. The mixture is then placed in lined (polytetrafluoroethylene) stainless steel pressure vessel and digested at a temperature for a time. Digestions are typically carried out at the autogenous pressure.

MeAPO MOLECULAR SIEVES

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,029. Members of this novel class of compositions have a three dimensional microporous crystal framework structure of MO$_2^{-2}$, AlO$_2^-$ and PO$_2^+$ tetrahedral units and have an essential empirical chemical composition, on an anhydrous basis, of:

$$mR: (M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3 maximum value in each case depending upon the molecular dimensions of the templating agent and the available void volume of the pore system of the particular metal aluminophosphate involved; "x", "y", and "z" represent the mole fractions of the metal "M" (i.e., magnesium, manganese, zinc and cobalt), aluminum and phosphorus, respectively, present as tetrahedral oxides, said mole fractions being such that they are representing the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the metal aluminophosphates of this invention, the values of "x", "y" and "z" in the formula above are representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The as-synthesized compositions are capable of withstanding 350° C. calcination in air for extended periods, i.e., at least 2 hours, without becoming amorphous. While it is believed that the M, Al and P framework constituents are present in tetrahedral coordination with oxygen, it is theoretically possible that some minor fraction of these framework constituents are present in coordination with five or six oxygen atoms. It is not, moreover, necessarily the case that all of the M, Al and/or P content of any given synthesized product be a part of the framework in the aforesaid types of coordination with oxygen. Some of each constituent may be merely occluded or in some as yet undetermined form and may or may not be structurally significant.

Since the term "metal aluminophosphate" is somewhat cumbersome, particularly in view of the need for numerous repetitions thereof in describing such compositions, the "short hand" reference "MeAPO" is employed hereinafter. Also in those cases where the metal "Me" in the composition is magnesium, the acronym MAPO is applied to the composition. Similarly, ZAPO, MnAPO, and CoAPO are applied to the compositions which contain zinc, manganese and cobalt, respectively. To identify the various structural species which make up each of the subgeneric classes MAPO, ZAPO, CoAPO and MnAPO, each species is assigned a number and is identified, for example, as ZAPO-5. MAPO-11. CoAPO 11 and so forth.

The term "essential empirical chemical composition" is meant to include the crystal framework and can include any organic templating agent present in the pore system, but does not include alkali metal or other ions which can be present by virtue of being contained in the reaction mixture or as a result of post-synthesis ion-exchange. Such ionic species, when present, function primarily as charge balancing ions for $AlO_2^-$ and/or $MO_2^{-2}$ tetrahedra not associated with $PO_2^+$ tetrahedra or an organic ion derived from the organic templating agent.

The metal aluminophosphates ("MeAPOs") are synthesized by hydrothermal crystallization from a reaction mixture containing reactive sources of the metal "M" alumina and phosphate, an organic templating, i.e., structure-directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature between 100° C. and 225° C., and preferably between 100° C. and 200° C. until crystals of the metal aluminophosphate product are obtained, usually a period of from 4 hours to 2 weeks. The product is recovered by any convenient method such as centrifugation or filtration.

In synthesizing the MeAPO compositions, it is preferred to employ a reaction mixture composition expressed in terms of molar ratios as follows:

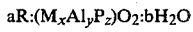

$$aR:(M_xAl_yP_z)O_2:bH_2O$$

wherein "R" is an organic templating agent; "a" has a value great enough to constitute an effective concentration of "R" and is within the range of >0 to 6; "b" has a value of from zero to 500, preferably 2 to 30; "M" represents a metal of the group zinc, magnesium, manganese and cobalt, "x" "y" and "z" represent the mole fractions, respectively, of "M" aluminum and phosphorus in the $(M_xAl_yP_z)O_2$ constituent, and each has a value of at least 0.01, the said points E, F, G, H, I, and J representing the following values for "x" "y" and "z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(M+Al+P)=(x+y+z)=1.00$ mole.

In forming the reaction mixture from which the metal aluminophosphates are crystallized the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[C_{14}H_{32}N_2)(OH)_2]_x$ wherein "x" has a value of at least 2 are also suitably employed. Both mono-, di- and triamines are advantageously utilized, either alone or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N dimethylbenzylamine; N-N-dimethylethanolamine; choline; N,N'-dimethylpiperazine; 1,4-diazabicyclo (2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di n butylamine; neopentylamine; di-n-pentylamine; isopropylamine; t-butylamine; ethylenediamine; pyrrolidine; and 2-imidazolidone. Not every templating agent will direct the formation of every species of metal aluminophosphate (MeAPO), i.e., a single templating agent can, with proper manipulation of the reaction conditions, direct the formation of several MeAPO compositions, and a given MeAPO composition can be produced using several different templating agents.

The preferred phosphorus source is phosphoric acid, but organic phosphates such as triethylphosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are not preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The metals zinc, cobalt, magnesium and manganese can be introduced into the reaction system in any form which permits the formation in situ of reactive divalent ions of the respective metals. Advantageously salts, oxides or hydroxides of the metals are employed such as cobalt chloride hexahydrate, alpha cobaltous iodide, cobaltous sulfate, cobalt acetate, cobaltous bromide, cobaltous chloride, zinc acetate, zinc bromide, zinc formate, zinc iodide, zinc sulfate heptahydrate, magnesium acetate, magnesium bromide, magnesium chloride, magnesium iodide, magnesium nitrate, magnesium sulfate, manganous acetate, manganous bromide, manganous sulfate, and the like.

While not essential to the synthesis of MeAPO compositions, it has been found that in general, stirring or other moderate agitation of the reaction mixture and/or seeding the reaction mixture with seed crystals of either the MeAPO species to be produced or a topologically similar aluminophosphate or aluminosilicate composition, facilitates the crystallization procedure.

After crystallization the MeAPO product is isolated and advantageously washed with water and dried in air. The as-synthesized MeAPO contains within its internal pore system at least one form of the templating agent employed in its formation. Most commonly the organic moiety is present, at least in part, as a charge-balancing cation as is generally the case with as synthesized aluminosilicate zeolites prepared from organic-containing reaction systems. It is possible, however, that some or all of the organic moiety is an occluded molecular species in a particular MeAPO species. As a general rule, the templating agent, and hence the occluded organic species, is too large to move freely through the pore system of the MeAPO product and must be removed by calcining the MeAPO at temperatures of 200° C. to 700° C. to thermally degrade the organic species. In a few instances the pores of the MeAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein and in the claims does not include the condition of the MeAPO phase wherein the organic moiety occupying the intracrystalline pore system as a result of the hydrothermal crystallization process has been reduced by post-synthesis treatment such that the value of "m" in the composition formula:

mR: $(M_xAl_yP_z)O_2$ has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the syntheses process as a templating agent. For the purposes of this application, however, this alcohol is arbitrarily omitted from the class of templating agents, even if it is present in the as synthesized MeAPO material.

Since the MeAPO compositions are formed from $AlO_2$, $PO_2$, and $MO_2$, tetrahedral units which respectively, have a net charge of $-1$, $+1$, and $-2$ the matter of cation exchangeability is considerably more complicated than in the case of zeolitic molecular sieves in which, ideally, there is a stoichiometric relationship between $AlO_2$ tetrahedra and charge balancing cations. In the MeAPO compositions, an $AlO_2^-$ tetrahedron can be balanced electrically either by association with a $PO_2^+$ tetrahedron or a simple cation such as an alkali metal cation, a cation of the metal "M" present in the reaction mixture, or an organic cation derived from the templating agent. Similarly an $MO_2^{-2}$ tetrahedron can be balanced electrically by association with $PO_2^+$ tetrahedra, a cation of the metal "M", organic cations derived from the templating agent, or other divalent or polyvalent metal cations introduced from an extraneous source. It has also been postulated that non-adjacent $AlO_2^-$ and $PO_3^+$ tetrahedral pairs can be balanced by $Na^+$ and $OH^-$, respectively [Flanigen and Grose, Molecular Sieve Zeolites-I, ACS, Washington, D.C. (1971)].

FAPO MOLECULAR SIEVES

Ferroaluminophosphates are disclosed in U.S. Pat. No. 4,500,561, incorporated herein by reference, and comprise a three-dimensional microporous crystal framework structrue of $AlO_2$, $FeO_2$, and $PO_2$ tetrahedral units and have an essential empirical chemical composition, on an anhydrous basis, of:

mR: $(Fe_xAl_yP_z)O_2$ wherein "R" represents at least one organic templating agent present in the intracrystalline pore system; "m" represents the moles of "R" present per mole of $(Fe_xAl_yP_z)O_2$ and has a value of from zero to 0.3, the maximum value in each case depending upon the molecular dimensions of the templating agent and the available void volume of the pore system of the particular ferroaluminophosphate involved; "x", "y" and "z" represent the mole fractions of iron, aluminum and phosphorus, respectively, present as tetrahedral oxides, representing the following values for "x", "y" and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the ferroaluminophosphates the values of "x", "y" and "z" in the formula above are representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The iron of the $FeO_2$ structural units can be in either the ferric or ferrous valence state, depending largely upon the source of the iron in the synthesis gel. Thus, an $FeO_2$ tetrahedron in the structure can have a net charge of either $-1$ or $-2$. While it is believed that the Fe, Al and P framework constituents are present in tetrahedral coordination with oxygen (and are referred to herein as such), it is theoretically possible that some minor fraction of these framework constituents are present in coordination with five or six oxygen atoms. It is not, moreover, necessarily the case that all of the Fe, Al and/or P content of any given synthesized product is a part of the framework in the aforesaid types of coordinaiton with oxygen. Some of each constituent may be merely occluded or in some as yet undetermined form, and may or may not be structually significant.

For convenience in describing the ferroaluminophosphates, the "short-hand" acronym "FAPO" is sometimes employed hereinafter. To identify the various structural species which make up the generic class FAPO, each species is assigned a number and is identified, for example, as FAPO-11, FAPO-31 and so forth.

The term "essential empirical chemical composition" is meant to include the crystal framework and can include any organic templating agent present in the pore system, but does not include alkali metal or other ions which can be present by virtue of being contained in the reaction mixture or as a result of post-synthesis ion-exchange. Such ionic species, when present, function primarily as charge-balancing ions for $FeO_2^-$ and/or $AlO_2^{-2}$ tetrahedra, $FeO_2^{-2}$ tetrahedra associated with $PO_2^+$ tetrahedra or not associated with $PO_2^+$ tetrahedra or an organic ion derived from the organic templating agent.

The aforesaid ferroaluminophosphates are synthesized by hydrothermal crystallization from a reaction mixture containing reactive sources of iron oxide, alumina and phosphate, an organic templating, i.e., structure-directing, agent, preferably a compound of an element of Group VA of the Periodic Table, and optionally an alkali metal. The reaction mixture is placed in a sealed pressure vessel, preferably lined iwth an inert plastic material such as polytetrafluoroethylene and heated, preferably under autogenous pressure at a temperature of at least 100° C., and preferably between 100° C. and 250° C. until crystals of the metal aluminophosphate product are obtained, usually a period of from 2 hours to 2 weeks. The product is recovered by any convenient method such as centrifugation or filtration.

In synthesizing the FAPO compositions, it is preferred to employ reaction mixture composition expressed in terms of molar ratios as follows:

$$aR:(Fe_xAl_yP_z)O_2: bH_2O$$

wherein "R" is an organic templating agent; "a" has a value great enough to constitute an effective concentration of "R" and is within the range of >0 to 6; "b" has a value of from zero to 500, preferably 2 to 80; "x", "y" and "z" represent the mole fractions, respectively, of iron, aluminum and phosphorus in the $(Fe_xAl_yP_z)O_2$ constituent, and each has a value of at least 0.01, and representing the following values for "x", "y" and "z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(Fe+Al+P)=(x+y+z)=1.00$ mole.

In forming the reaction mixture from which the ferroaluminophosphates are crystallized, the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsen and antimony, preferably N or P and most preferably N, which compounds also contain at least one alkyl or aryl group having from 1 to 8 carbon atoms. Particulary preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[C_{14}H_{32}N_2] (OH)_2]_x$ wherein "x" has a value of at least 2 are also suitably employed. Both mono-, di- and triamines are advantageously utilized, either or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine; tri-n-propylamine; triethylamine; triethanolamine; piperidine; cyclohexylamine; 2-methylpyridine; N,N-dimethylbenzylamine; N-N-dimethylethanolamine; choline; N,N'-dimethylpiperazine; 1,4 diazabicyclo (2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of ferroaluminophosphate (FAPO), i.e., a single templating agent can, with proper manipulation of the reaction conditions, direct the formation of several FAPO compositions, and a given FAPO composition can be produced using several different templating agents.

The phosphorus source is preferably phosphoric acid, but organic phosphates such as triethylphosphate have been found satisfactory, and so also have crystalline or amorphous aluminophosphates such as the AlPO4 composition of U.S. Pat. No. 4,310,440. Organo-phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are not preferred.

The aluminum source is preferably either an aluminum alkoxide, such as aluminum isoproxide, or peseudoboehmite. The crystalline or amorphous aluminophosphates which are a suitable source of phosphorus are, of course, suitable sources of aluminum. Other sources of aluminum used in zeolite synthesis, such as gibbsite, sodium aluminate and aluminum trichloride, can be employed but are not preferred.

Iron can be introduced into the reaction system in any form which permits the formation in situ of reaction ferrous of ferric ions. Advantageously iron salts, oxides or hydroxides are employed such as iron sulfate, iron acetate, iron nitrate, or the like. Other sources such as a freshly precipitated iron oxide γ-FeOOH, are also suitable.

While not essential to the synthesis of FAPO compositions, it has been found that in general, stirring or other moderate agitation of the reaction mixture and/or seeding the reaction mixture with seed crystals of either the FAPO species to be produced or a topologically similar aluminophosphate or aluminosilicate composition, facilitates the crystallization procedure.

After crystallization the FAPO product is isolated and advantgageously washed with water and dried in air. The as-synthesized FAPO contains within its internal pore system at least one form of the templating agent employed in its formation. Most commonly the organic moiety is present, at least in part, as a charge-balancing cation as is generally the case with as-synthesized aluminosilicate zerolites prepared from organic-containing reaction systems. It is possible, however, that some or all of the organic moiety is an occuded molecular species in a particular FAPO species. As a general rule, the templating agent, and hence the occluded organic species, is too large to move freely through the pore system of the FAPO product and must be removed by calcining the FAPO at temperatures of 200° C. to 700° C. to thermally degrade the organic species. In a few instances the pores of the FAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein and in the claims does not include the condition of the FAPO phase wherein the organic moiety occupying the intracrystalline pore system as a result of the hydrothermal crystallization process has been reduced by post-synthesis treatment such that the value of "m" in the formula:

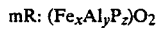

mR: $(Fe_xAl_yP_z)O_2$ has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the syntheses process as a templating agent. For the purposes of this applicaiton, however, this alcohol is arbitrarily omitted from the class of templating agents, even if it is present in the as-synthesized FAPO material.

Since the FAPO compositions are formed from $AlO_2^-$, $PO_2^-$, and /or $FeO_2^{-2}$ units the matter of cation exchangeability is considerably more complicated than in the case of zeolitic molecular sieves in which, ideally, there is a stoichiometric relationship between $AlO_2$ tetrahedra and charge-balancing cations. In the FAPO compositions, and $AlO_2^-$ tetrahedron can be balanced electrically either by association with a $PO_2^+$ tetrahedron or a simple cation such as an alkali metal cation, a $Fe^{+2}$ or $Fe^{+3}$ cation present in the reaction mixture, or an organic cation dervied from the templating agent. Similarly an $FeO_2^-$ or $FeO_2^{-2}$ tetrahedron can be balanced electrically by association with $PO_2^+$ tetrahedron, a $Fe^{+2}$ or $Fe^{+3}$ cation, organic cations derived from the templating agent, or other metal cation introduced from an extraneous source. It has also been postulated that non-adjacent $AlO_2^-$ and $PO_2^+$ tetrahedral pairs can be balanced by $Na^+$ and $OH^-$, respectively [Flanigen and Grose, Molecular Sieve Zeolites-I, ACS, Washington D.C. (1971)].

TAPO MOLECULAR SIEVES

TAPO molecular sieves are disclosed in U.S. Pat. No. 4,500,561, incorporated herein by reference, and comprise a three-dimensional microporous crystal framework structure of $[TiO_2]$, $[AlO_2]$ and $[PO_2]$ tetrahedral units has a unit empricical formula on an anhydrous basis of:

mR: $(Ti_xAl_yP_z)O_2$ wherein "R" represents at least one organic templating agent present in the intracrystalline pore system; "m" represents the moles of "R" present per mole of $(Ti_xAl_yP_z)O_2$ and has a value of between zero and obout 5.0 the maximum value in each case depending upon the molecular dimensions of the templating agent and the available void volume of pore system of the particular titanium molecular sieve; "x", "y" and "z" represent the mole fractions of titanium, aluminum and phosphorus, respectively, present as tetrahedral oxides, representing the following values for "x", "y" and "z":

| Point | Mole Fraction | | |
|---|---|---|---|
| | x | y | z |
| A | 0.001 | 0.45 | 0.549 |
| B | 0.88 | 0.01 | 0.11 |
| C | 0.98 | 0.01 | 0.01 |
| D | 0.29 | 0.70 | 0.01 |
| E | 0.001 | 0.70 | 0.299 |

The parameters "x", "y" and "z" are preferably within the following values for "x", "y" and "z":

| Point | Mole Fraction | | |
|---|---|---|---|
| | x | y | z |
| a | 0.002 | 0.499 | 0.499 |
| b | 0.20 | 0.40 | 0.40 |
| c | 0.20 | 0.50 | 0.30 |
| d | 0.10 | 0.60 | 0.30 |
| e | 0.002 | 0.60 | 0.398 |

The titanium-containing molecular sieves are referred to hereinafter, solely for point of reference herein as "TAPO" molecular sieves, or as "TAPOs" if the reference is to the class as a whole. This designation is simply made for the sake of convenient reference herein and is not meant to designate a particular structure for any given TAPO molecular sieve. The members of the class of TAPOs employed hereinafter in the examples will be characterized simply by referring to such members as TAPO-5, TAPO-11, etc, i.e., a particular species will be referred to as TAPO-n where "n" is a number specific to a given class member as its preparation is reported herein. This designation is an arbitrary one and is not intended to denote structural relationship to another material(s) which may also be characterized by a numbering system.

The term "unit empirical formula" is used herein according to its common meaning to designate the simplest formula which gives the relative number of moles of titanium, aluminum and phosphorus which form the $[TiO_2]$, $[PO_2]$ and $[AlO_2]$ tetrahedral unit within a titanium-containing molecular sieve and which forms the molecular framework of the TAPO composition(s). The unit empirical formula is given in terms of titanium, aluminum and phosphorus as shown in Formula (1), above, and does not include other compounds, cations or anions which may be present as a result of the preparation or the existence of other impurities or materials in the bulk composition not containing the aforementioned tetrahedral unit. The amount of template R is reported as part of the composition when the as-synthesized unit empirical formula is given, and water may also be reported unless such is defined as the anhydrous form. For convenience, coefficient "m" for template "R" is reported as a value that is normalized by dividing the number of moles of organic by the total moles of titanium, aluminum and phosphorus.

The unit empirical formula for a TAPO may be given on an "as-synthesized" basis or may be given after an "as synthesized" TAPO composition has been subjected to some post treatment process, e.g., calcination. The term "as synthesized" herein shall be used to refer to the TAPO composition(s) formed as a result of the hydrothermal crystallization but before the TAPO composition has been subjected to post treatment to remove any volatile components present therein. The actual value of "m" for a post-treated TAPO will depend on several factors (including: the particular TAPO, template, severity of the post-treatment in terms of its ability to remove the template from the TAPO, the proposed application of the TAPO composition, and etc.) and the value for "m" can be within the range of values as defined for the as synthesized TAPO compositions although such is generally less than the as-synthesized TAPO unless such post-treatment process adds template to the TAPO so treated. A TAPO composition which is in the calcined or other post-treatment form generally has an empirical formula represented by Formula (1), except that the value of "m" is generally less than about 0.02. Under sufficiently severe post-treatment conditions, e.g., roasting in air at high temperature for long periods (over 1 hr.), the value of "m" may be zero (0) or, in any event, the template, R, is undetectable by normal analytical procedures.

The TAPO molecular sieves are generally further characterized by an intracrystalline adsorption capacity for water at 4.6 torr and about 24° C. of about 3.0 weight percent. The adsorption of water has been observed to be completely reversible while retaining the same essential framework topology in both the hydrated and dehydrated state. The term "essential framework topology" is meant to designate the spatial arrangement of the primary bond linkages. A lack of change in the framework topology indicates that there is no disruption of these primary bond linkages.

The TAPO molecular sieves are generally synthesized by hydrothermal crystallization from a reaction mixture comprising reactive sources of titanium, aluminum and phosphorus, and one or more organic templating agents. Optionally, alkali metal (s) may be present in the reaction mixture. The reaction mixture is placed in a pressure vessel, preferably lined with an inert plastic material, such as polytetrafluoroethylene, and heated, preferably under the autogenous pressure, at a temperature of at least about 100° C., and preferably between 100° C. and 250° C., until crystals of the molecular sieve product are obtained, usually for a period of from 2 hours to 2 weeks. While not essential to the synthesis of the TAPO molecular sieves, it has been found that in general stirring or other moderate agitation of the reaction mixture and/or seeding the reaction mixture with seed crystals of either the TAPO to be produced, or a topologically similar composition, facilitates the crystallization procedure. The product is recovered by any convenient method such as centrifugation or filtration.

After crystallization the TAPO(s) may be isolated and washed with water and dried in air. As a result of the hydrothermal crystallization, the as-synthesized TAPO contains within its intracrystalline pore system at least one form of the template employed in its formation. Generally, the template is a molecular species, but it is possible, steric considerations permitting, that at least some of the template is present as a charge-balancing cation. Generally the template is too large to move freely through the intracrystalline pore system of the formed TAPO and may be removed by a post-treatment process, such as by calcining the TAPO at temperatures of between about 200° C. and to about 700° C. so as to thermally degrade the template or by employing some other post-treatment process for removal of at least part of the template from the TAPO. In some instances the pores of the TAPO are sufficiently large to permit transport of the template, and, accordingly, complete or partial removal thereof can be accomplished by conventional desorption procedures such as carried out in the case of zeolites.

The TAPOs are preferably formed from a reaction mixture having a mole fraction of alkali metal cation which is sufficiently low that it does not interfere with the formation of the TAPO composition. The TAPO compositions are generally formed from a reaction mixture containing reactive sources of $TiO_2$, $Al_2O_3$, and $P_2O_5$ and an organic templating agent, said reaction mixture comprising a composition expressed in terms of molar oxide ratios of:

$$fR_2O:(Ti_xAl_yP_z)O_2:g\ H_2O$$

wherein "R" is an organic templating agent; "f" has a value large enough to constitute an effective amount of "R" said effective amount being that amount which form said TAPO compositions; "g" has a value of from zero to 500; "x", "y" and "z" represent the mole fractions, respectively of titanium, aluminum and phosphorus in the $(Ti_xAl_yP_z)O_2$ constituent, and each has a value of at least 0.001 and being within the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

Although the TAPO compositions will form if higher concentrations of alkali metal cation are present, such reaction mixtures are not generally preferred. A reaction mixture, expressed in terms of molar oxide ratios, comprising the following bulk composition is preferred:

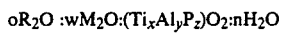

$oR_2O : wM_2O : (Ti_xAl_yP_z)O_2 : nH_2O$ wherein "R" is an organic template; "o" has a value great enough to constitute an effective concentration of "R" and is preferably within the range of from greater than zero (0) to about 5.0; "M" is an alkali metal cation; "w" has a value of from zero to 2.5; "n" has a value between about zero (0) and about 500; "x", "y" and "z" represent the mole fractions, respectively, of titanium, aluminum and phosphorus in $(Ti_xAl_yP_z)O_2$: "x", "y" and "z" represent the mole fractions, respectively of titanium, aluminum and phosphorus in the $(Ti_xAl_yP_z)O_2$ constituent, and each has a value of at least 0.001 and being within the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

When the TAPOs are synthesized by this method the value of "m" in Formula (1) is generally above about 0.02.

Though the presenc of alkali metal cations is not preferred, when they are present in the reaction mixture it is preferred to first admix at least a portion (e.g., at least about 10 weight percent) of each of the aluminum and phosphorus sources in the substantial absence (e.g., preferably less than about 20 percent of the total weight of the aluminum source and phosphorus source) of the titanium source. This procedure avoids adding the phosphorus source to a basic reaction mixture containing the titanium source and aluminum source, (as was done in most of the published attempts to substitute isomorphously [PO₂] tetrahedra for [SiO₂] tetrahedra in zeolitic structures). Although the reaction mechanism is by no means clear at this time, the function of the template may be to favor the incorporation of [PO₂] and [AlO₂] tetrahedra in the framework structures of the crystalline products with [TiO₂] tetrahedra isomorphously replacing [PO₂] tetrahedra.

The reaction mixture from which these TAPOs are formed contains one or more organic templating agents (templates) which can be most any of those heretofore proposed for use in the synthesis of aluminosilicates and aluminophosphates. The template preferably contains at least one element of Group VA of the Periodic Table, particularly nitrogen, phosphorus, arsenic and/or antimony, more preferably nitrogen or phosphorus and most preferably nitrogen and are of the formula $R_4X^+$ wherein X is selected from the group consisting of nitrogen, phosphorus, arsenic and/or antimony and R may be hydrogen, alkyl, aryl, aralkyl, or alkylaryl group and is preferably aryl or alkyl containing between 1 and 8 carbon atoms, although more than eight carbon atoms may be present in "R" of group of the template. Nitrogen-containing templates are preferred, including amines and quaternary ammonium compounds, the latter being represented generally by the formula $R'_4N^+$ wherein each R' is an alkyl, aryl, alkylaryl, or araalkyl group; wherein R' preferably contains from 1 to 8 carbon atoms or higher when R' is alkyl and greater than 6 carbon atoms when R' is otherwise, as hereinbefore discussed. Polymeric quaternary ammonium salts such as $[(C_{14}H_{32}N_2)(OH)_2]_x$ wherein "x" has a value of at least 2 may also be employed. The mono-, di- and triamines, including mixed amines, may also be employed as templates either alone or in combination with a quaternary ammonium compound or another template. The exact relationship of various templates when concurrently employed is not clearly understood. Mixtures of two or more templating agents can produce either mixtures of TAPOs or in the instance where one template is more strongly directing than another template the more strongly directing template may control the course of the hydrothermal crystallization wherein the other template serving primarily to establish the pH conditions of the reaction mixture.

Representative templates include tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N-dimethylbenzylamine; N,N-diethylethanolamine; dicyclohexylamine; N,N-dimethylethanolamine; 1,4-diazabicyclo (2,2,2) octane; N-methyldiethanolamine, N-methylethanolamine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. As will be readily apparent from the illustrative examples set forth hereinafter, not every template will produce every TAPO composition although a single template can, with proper selection of the reaction conditions, cause the formation of different TAPO compositions, and a given TAPO composition can be produced using different templates.

In those instances where an aluminum alkoxide is the reactive aluminum source, the corresponding alcohol is necessarily present in the reaction mixture since it is a hydrolysis product of the alkoxide. It has not as yet been determined whether this alcohol participates in the synthesis process as a templating agent, or in some other function and, accordingly, is not reported as a template in the unit formula of the TAPOs, although such may be acting as templates.

Alkali metal cations, if present in the reaction mixture, may facilitate the crystallization of certain TAPO phases, although the exact function of such cations, when present, in crystallization, if any, is not presently known. Alkali cations present in the reaction mixture generally appear in the formed TAPO composition, either as occluded (extraneous) cations and/or as structural cations balancing net negative charges at various sites in the crystal lattice. It should be understood that although the unit formula for the TAPOs does not specifically recite the presence of alkali cations they are not excluded in the same sense that hydrogen cations and/or hydroxyl groups are not specifically provided for in the traditional formulae for zeolitic aluminosilicates.

Most any reactive titanium source may be employed herein. The preferred reactive titanium sources include titanium alkoxides, water-soluble titanates and titanium chelates.

Most any reactive phosphorous source may be employed. Phosphoric acid is the most suitable phosphorus source employed to date. Accordingly, other acids of phosphorus are generally believed to be suitable phosphorus sources for use herein. Organic phosphates such as triethyl phosphate have been found satisfactory and so also have crystalline or amorphous aluminophosphates such as the AlPO$_4$ compositions of U.S. Pat. No. 4,310,440. Organo-phosphorus compounds, such as tetrabutyl-phosphonium bromide have not, apparently, served as reactive sources of phosphorus, but these compounds do function as templating agents and may also be capable of being suitable phosphorus sources under proper process conditions (yet to be ascertained). Organic phosphorus compounds, e.g., esters, are believed to be generally suitable since they can generate acids of phosphorus in situ. Conventional phosphorus salts, such as sodium metaphosphate, may be used, at least in part as the phosphorus source, but they are not preferred.

Most any reactive aluminum source may be employed herein. The preferred reactive aluminum sources include aluminum alkoxides, such as aluminum isopropoxide, and pseudoboehmite. Crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but as generally not preferred.

Since the exact nature of the TAPO molecular sieves are not clearly understood at present, although all are believed to contain [TiO$_2$] tetrahedra in the three-dimensional microporous crystal framework structure, it is advantageous to characterize the TAPO molecular sieves by means of their chemical composition. This is due to the low level of titanium present in certain of the TAPO molecular sieves prepared to date which makes it difficult to ascertain the exact nature of the interaction between titanium, aluminum and phosphorus. As a result, although it is believed that titanium, [TiO$_2$], has substituted isomorphously for [AlO$_2$] or [PO$_2$] tetrahedra, it is appropriate to characterize certain TAPO compositions by reference to their chemical composition in terms of the mole ratios of oxides in the as-synthesized and anhydrous form as:

$$vR: pTiO_2:qAl_2O_3:rP_2O_5$$

wherein "R" represents at least one organic templating agent present in the intracrystalline pore system; "v" represents an effective amount of the organic templating agent to form said TAPO compositions and preferably has a value between and including zero and about 3.0; "p", "q" and "r" represent moles, respectively, of titanium, alumina and phosphorus pentaoxide, based on said moles being such that they are within the following values for "p", "q" and "r":

| Point | Mole Fraction | | |
|---|---|---|---|
| | p | q | r |
| A | 0.004 | 1.0 | 1.22 |
| B | 176 | 1.0 | 11.0 |
| C | 196 | 1.0 | 1.0 |
| D | 0.828 | 1.0 | 0.0143 |
| E | 0.003 | 1.0 | 0.427 |

The parameters "p", "q" and "r" are preferably within the following values for "p", "q" and "r":

| Point | Mole Fraction | | |
|---|---|---|---|
| | p | q | r |
| a | 0.008 | 1.0 | 1.0 |
| b | 1.0 | 1.0 | 1.0 |
| c | 0.80 | 1.0 | 0.60 |
| d | 0.333 | 1.0 | 0.50 |
| e | 0.067 | 1.0 | 0.663 |

ELAPO MOLECULAR SIEVES

"ELAPO" molecular sieves are a class of crystalline molecular sieves in which at least one element capable of forming a three-dimensional microporous framework form crystal framework structures of AlO$_2^-$, PO$_2^+$ and MO$_2^n$ tetrahedral oxide units wherein "MO$_2^n$" represents at least one different element (other than Al or P) present as tetrahedral oxide units "MO$_2^n$" with charge "n" where "n" may be $-3, -2, -1, 0$ or $+1$. The members of this novel class of molecular sieve compositions have crystal framework structures of AlO$_2^-$, PO$_2^+$ and MO$_2^n$ tetrahedral units and have an empirical chemical composition on an anhydrous basis expressed by the formula:

$$mR: (M_xAl_yP_z)O_2$$

wherein "R" represents at least one organic templating agent present in the intracrystalline pore system; "m" represents the molar amount of "R" present per mole of $(M_xAl_yP_z)O_2$; "M" represents at least one element capable of forming framework tetrahedral oxides; and "x", "y" and "z" represent the mole fractions of "M", aluminum and phosphorus, respectively, present as tetrahedral oxides. "M" is at least one different element (M$_1$) such that the molecular sieves contain at least one framework tetrahedral units in addition to AlO$_2^-$ and PO$_2^{30}$. "M" is at least one element selected from the group consisting of arsenic, beryllium, boron, chromium, allium, germanium and lithium, and when "M" denotes two elements the second element may be one of the aforementioned and/or is at least one element selected from the group consisting of cobalt, iron, magnesium, manganese, titanium and zinc. ELAPOs and their preparation are disclosed in European patent application Ser. No. 85104386.9, filed Apr. 11, 1985 (EPC publication No. 0158976, published Oct. 13, 1985, incorporated herein by reference) and No. 85104388.5, filed Apr. 11, 1985 (EPC publication No. 158349, published Oct. 16, 1985, incorporated herein by reference).

The ELAPO molecular sieves are generally referred to herein by the acronym or "ELAPO" to designate element(s) "M" in a framework of AlO$_2^-$, PO$_2^+$ and MO$_2^n$ tetrahedral oxide units. Actual class members will be identified by replacing the "EL" of the acronym with the elements present as MO$_2^n$ tetrahedral units. For example, "MgBeAPO" designates a molecular sieve comprised of AlO$_2^{31}$, PO$_2^+$, MgO$_2^{-2}$ and BeO$_2^{-2}$ tetrahedral units. To identify various structural species which make up each of the subgeneric classes, each species is assigned a number and is identified as "ELAPO-i" wherein "i" is an integer. The given species designation is not intended to denote a similarity in structure to any other species denominated by a similar identification system.

The ELAPO molecular sieves comprise at least one additional element capable of forming framework tetrahedral oxide units ($MO_2{}^n$) to form crystal framework structures with $AlO_2$ and $PO_2{}^+$ tetrahedral oxide units wherein "M" represents at least one element capable of forming tetrahedral units "$MO_2{}^n$", where "n" is $-3, -2, -1, 0$ or $+1$ and is at least one element selected from the group consisting of arsenic, beryllium, boron, chromium, gallium, germanium and lithium. When "M" denotes two elements "M" may also be at least one element selected from the group consisting of cobalt, iron, magnesium, manganese, titanium and zinc. For example, in each instance "M" includes at least one of the first group of elements, e.g., As, Be, etc., and when two or more elements are present, the second and further elements may be selected from the first group of elements and/or the second group of elements, as above discussed.

The ELAPO molecular sieves have crystalline three-dimensional microporous framework structures of $AlO_2{}^-$, $PO_2{}^+$ and $MO_2{}^n$ tetrahedral units and have an empirical chemical composition on an anhydrous basis expressed by the formula:

mR: $(M_xAl_yP_z)O_2$;

wherein "R" represents at least one organic templating agent present in the intracrystalline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, chromium, gallium, germanium and lithium. When "M" includes an additional element such additional elements "M" may be at least one element selected from the group consisting of cobalt, iron, magnesium, manganese, titanium, and zinc.

The relative amounts of element(s) "M", aluminum and phosphorus are expressed by the empirical chemical formula (anhydrous):

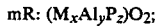

mR: $(M_xAl_yP_z)O_2$;

where "x", "y" and "z" represent the mole fractions of said "M", aluminum and phosphorus. The individual mole fractions of each "M" (or when M denotes two or more elements, $M_1$, $M_2$, $M_3$, etc.) may be represented by "$x_1$", "$x_2$", "$x_3$", etc. wherein "$x_1$", "$x_2$", and "$x_3$", and etc. represent the individual mole fractions of elements $M_1$, $M_2$, $M_3$, and etc. for "M" as above defined. The values of "$x_1$", "$x_2$", "$x_3$", etc. are as defined for "x", hereinafter, where "$x_1$"+"$x_2$"+"$x_3$" ... ="x" and where $x_1$, $x_2$, $x_3$, etc. are each at least 0.01.

The ELAPO molecular sieves have crystalline three-dimensional microporous framework structures of $Mo_2{}^n$, $AlO_2{}^-$ and $PO_2{}^+$ tetrahedral units having an empirical chemical composition on an anhydrous basis expressed by the formula:

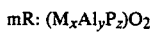

mR: $(M_xAl_yP_z)O_2$ wherein "R" represents at least one organic templating agent present in the intracrystalline pore system; "m" represents a molar amount of "R" present per mole of $(M_xAl_yP_z)O_2$ and has a value of zero to about "M" represents at least one different element (other than Al or P) capable of forming framework tetrahedral oxides, as hereinbefore defined, and "x", "y" and "z" represent the mole fractions of "M", aluminum and phosphorus, respectively, present as tetrahedral oxides; said mole fractions "x", "y" and "z" being generally defined as within the following values for "x", "y", and "z":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred sub-class of the ELAPOs of this invention, the values of "x", "y" and "z" in the formula above are within the following values for "x", "y" and "z":

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

ELAPO compositions are generally synthesized by hydrothermal crystallization from a reaction mixture containing reactive sources of the elements "M", aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the ELAPO product are obtained, usually a period of from several hours to several weeks. Typical crystallization times are from about 2 hours to about 30 days with from about 2 hours to about 20 days being generally employed to obtain crystals of the ELAPO products. The product is recovered by any convenient method such as centrifugation or filtration.

In synthesizing the ELAPO compositions of the instant invention, it is preferred to employ a reaction mixture composition expressed in terms of the molar ratios as follows:

aR: $(M_xAl_yP_z)O_2$: $bH_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; "M" represents at least one element, as above described, capable of forming tetrahedral oxide framework units, $MO_2{}^n$, with $AlO_2{}^-$ and $PO_2{}^+$ tetrahedral units; "n" has a value of $-3, -2, -1, 0$ or $+1$; and "x", "y" and "z" represent the mole fractions of "M", aluminum and phosphorus, respectively, "y" and "z" each have a value of at least 0.01 and "x" has a value of at least 0.01 with each element "M" having a mole fraction of at least 0.01. The mole fractions "x", "y" and "z" are preferably within the following values for "x", "y" and "z":

| Point | Mole Fraction | | |
|---|---|---|---|
| | x | y | z |
| F | 0.01 | 0.60 | 0.39 |
| G | 0.01 | 0.39 | 0.60 |
| H | 0.39 | 0.01 | 0.60 |
| I | 0.98 | 0.01 | 0.01 |
| J | 0.39 | 0.60 | 0.01 |

In the foregoing expression of the reaction composition, the reactants are normalized with respect to a total of (M+Al+P)=(x+y+z)=1.00 mole, whereas in many of the working examples appearing hereinafter the reaction mixtures are expressed in terms of molar oxide ratios and may be normalized to 1.00 mole of $P_2O_5$. This latter form is readily converted to the former form by routine calculations by dividing the total number of moles of "M", aluminum and phosphorus into the moles of each of "M", aluminum and phosphorus. The moles of template and water are similarly normalized by dividing the total moles of "M", aluminum and phosphorus.

In forming the reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, guaternary phosphonium compounds and guaternary ammonium compounds, the latter two being represented generally by the formula $R_4X^+$ wherein "X" is nitrogen or phosphorus and each R is an alkyl or aryl group containing from 1 to 8 carbon atoms. Polymeric guaternary ammonium salts such as $[(C_{14}H_{32}N_2)(OH)_2]_x$ wherein "x" has a value of at least 2 are also suitably employed. The mono, di-and tri-amines are advantageously utilized, either alone or in combination with a quaternary ammonium compound or other templatine compound. Mixtures of two or more templatine agents can either produce mixtures of the desired ELAPOs or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; tetrapentylammonium ion; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2,) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2-octane ion; di-n-butylamine, neopentylamine; di-n-pentylamine; isopropylamine; t-butylamine; ethylenediamine; pyrrolidine; and 2-imidazolidone. Not every templating agent will direct the formation of every species of ELAPO, i.e., a single templating agent can, with proper manipulation of the reaction conditions, direct the formation of several ELAPO compositions, and a given ELAPO composition can be produced using several different templating agents.

The phosphorus source is preferably phosphoric acid, but organic phosphates such as triethyl phosphate may be satisfactory, and so also may crystalline or amorphous aluminophosphates such as the $AlPO_4$ composition of U.S. Pat. No. 4,310,440. Organo phosphorus compounds, such as tetrabutylphosphonium bromide, do not apparently serve as reactive sources of phosphorus, but these compounds may function as templating agents. Conventional phosphorus salts such as sodium metaphosphate, may be used, at least in part, as the phosphorus source, but are not preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The element(s) "M" can be introduced into the reaction system in any form which permits the formation in situ of reactive form of the element, i.e., reactive to form the framework tetrahedral oxide unit of the element. The organic and inorganic salts, of "M" such as oxides, alkoxides, hydroxides, halides and carboxylates, may be employed including the chlorides, bromides, iodides, nitrates, sulfates, acetates, formates, ethoxides, propoxides and the like.

While not essential to the synthesis of ELAPO compositions, stirring or other moderate agitation of the reaction mixture and/or seeding the reaction mixture with seed crystals of either the ELAPO species to be produced or a topologically similar species, such as aluminophosphate, aluminosilicate or molecular sieve compositions, facilitates the crystallization procedure.

After crystallization the ELAPO product may be isolated and advantageously washed with water and dried in air. The as-synthesized ELAPO generally contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular ELAPO species. As a general rule the templating agent, and hence the occluded organic species, is too large to move freely through the pore system of the ELAPO product and must be removed by calcining the ELAPO at temperatures of 200° C. to 700° C. to thermally degrade the organic species. In a few instances the pores of the ELAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the ELAPO phase wherein the organic moiety occupying the intracrystalline pore system as a result of the hydrothermal crystallization process has been reduced by post-synthesis treatment such that the value of "m" in the composition formula:

mR: $(M_xAl_yP_z)O_2$ has a value of less than 0.02. The other symbols of the formula are as defined hereinabove. In those preparations in which an alkoxide is employed as the source of element "M", aluminum or phosphorus, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as synthesized ELAPO material.

Since the present ELAPO compositions are formed from $MO_2^n$, $AlO_2$, and $PO_2^+$ tetrahedral oxide units which, respectively, have a net charge of "n", (where "m" may be $-3$, $-2$, $-1$, 0 or $+1$), $-1$ and $+1$, the matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a proton (H+), a cation of "M" present in the reaction mixture, or an organic cation derived from the templating agent. Similarly an $MO_2^n$ tetrahedron, where "n" is negative, can be balanced electrically by association with $PO_2^+$ tetrahedra, a cation of "M" present in the reaction mixture, organic cations derived from the templating agent, a simple cation such as an alkali metal cation, or other divalent or polyvalent metal cation, a proton (H+), anions or cations introduced from an extraneous source. It has also been postulated that non-adjacent $AlO_2^-$ and $PO_2^+$ tetrahedral pairs can be balanced by Na+ and OH− respectively [Flanigen and Grose, Molecular Sieve Zeolites-I, ACS, Washington, D.C. (1971)].

SILICOALUMINOPHOSPHATE MOLECULAR SIEVES

The preferred NZMSs, to date, are the silicoaluminophosphate molecular sieves described in U.S. Pat. No. 4,440,871. The use of such catalysts in reforming catalysts or as components in heretofore employed reforming/dehydrocyclization catalysts provides improved catalysts and provide products characterized by an improved selectivity to iso-products and provides improved activity in reforming/dehydrocyclization reactions.

The silicoaluminophosphate molecular sieves of U.S. Pat, No. 4,440,871 are disclosed as microporous crystalline silicoaluminophosphates, the pores of which are uniform and have nominal diameters of greater than about 3 Angstroms and whose essential empirical chemical composition in the as-synthesized and anhydrous form is:

mR: $(Si_xAl_yP_z)O_2$ wherein "R" represents at least one organic templating agent present in the intracrystalline pore system; "m" represents the moles of "R" present per mole of $(Si_xAl_yP_z)O_2$ and has a value of from 0.02 to 0.3; "x", "y" and "z" represent the mole fractions of silicon, aluminum and phosphorus, respectively, present as tetrahedral oxides, said mole fractions being such that they are within the pentagonal compositional area defined by points A, B, C, D and E of the ternary diagram of FIG. 5 and are preferably within the pentagonal compositional area defined by points a, b, c, d and e of FIG. 6. The SAPO molecular sieves of U.S. Pat. No. 4,440,871 are also described as silicoaluminophosphates having a three-dimensional microporous framework structure of $PO_2+$, $AlO_2+$ and $SiO_2$ tetrahedral units, and whose essential empirical chemical composition on an anhydrous basis is:

mR: $(Si_xAl_yP_z)O_2$ wherein "R" represents at least one organic templating agent present in the intracrystalline pore system; "m" represents the moles of "R" present per mole of $(Si_xAl_yP_z)O_2$ and has a value of from zero to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 5, said silicoaluminophosphate having a characteristic X-ray powder diffraction pattern which contains at least the d-spacings set forth below in any one of Tables I, III, V, VII, IX, XIII, XVII, XXI, XXIII or XXV of U.S. Pat. No. 4,440,871. Further, the as-synthesized crystalline silicoaluminophosphates of U.S. Pat. No. 4,440,871 may be calcined at a temperature sufficiently high to remove at least some of any organic templating agent present in the intracrystalline pore system as a result of such synthesis. The silicoaluminophosphates of U.S. Pat. No. 4,440,871 are generally referred to therein as "SAPO", as a class, or as "SAPO-n" wherein "n" is an integer denoting a particular SAPO as its preparation is reported in U.S. Pat. No. 4,440,871. The preparation of the SAPOs is disclosed in U.S. Pat. No. 4,440,871, incorporated herein by reference.

MP-SAPOs characterized by the aforementioned isobutane and triethylamine adsorption characteristics include SAPO-11, SAPO-31, SAPO-40 and SAPO-41.

The species SAPO-11 as referred to herein is a silicoaluminophosphate material having a three-dimensional microporous crystal framework structure of $PO_2+$, $AlO_2-$ and $SiO_2$ tetrahedral units, and whose essential empirical chemical composition on an anhydrous basis is:

mR: $(Si_xAl_yP_z)O_2$ wherein "R" represents at least one organic templating agent present in the intracrystalline pore system; "m" represents the moles of "R" present per mole of $(Si_xAl_yP_z)O_2$ and has a value of from zero to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 5, and preferably within the area bounded by points a, b, c, d and e on the ternary diagram which is FIG. 6, said silicoaluminophosphate having a characteristic X-ray powder diffraction pattern which contains at least the d-spacings set forth below:

| SAPO-11 | | | |
|---|---|---|---|
| $2\theta$ | | d(Å) | Relative Intensity |
| 9.4–9.65 | | 9.41–9.17 | m |
| 20.3–20.6 | | 4.37–4.31 | m |
| 21.0–21.3 | | 4.23–4.17 | vs |
| 21.1–22.35 | | 4.02–3.99 | m |
| 22.5–22.9 | (doublet) | 3.95–3.92 | m |
| 23.15–23.35 | | 3.84–3.81 | m–s |

The species SAPO-31 as referred to herein is a silicoaluminophosphate having a three-dimensional microporous crystal framework structure of $PO_2^+$, $AlO_2^-$ and $SiO_2$ tetrahedral units, and whose essential empirical chemical composition on an anhydrous basis is:

mR: $(Si_xAl_yP_z)O_2$ wherein "R" represents at least one organic templating agent present in the intracrystalline pore system; "m" represents the moles of "R" present per mole of $(Si_xAl_yP_z)O_2$ and has a value of from zero to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 5, and preferably within the area bounded by points a, b, c, d and e on the ternary diagram which is FIG. 6, said silicoaluminophosphate having a characteristic X-ray powder diffraction pattern which contains at least the d-spacings set forth below:

| SAPO-31 | | |
|---|---|---|
| $2\theta$ | d(Å) | Relative Intensity |
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

The species SAPO-41 as referred to herein is a silicoaluminophosphate having a three-dimensional microporous crystal framework structure of $PO_2^+$, $AlO_2^-$ and $SiO_2$ tetrahedral units, and whose essential empirical chemical composition on an anhydrous basis is:

mR: $(Si_xAl_yP_z)O_2$ wherein "R" represents at least one organic templating agent present in the intracrystalline pore system; "m" represents the moles of "R" present per mole of $(Si_xAl_yP_z)O_2$ and has a value of from zero to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 5, or preferably within the area bounded by points a, b, c, d and e on the ternary diagram which is FIG. 6, said silicoaluminophosphate having a characteristic X-ray powder diffraction pattern which contains at least the d-spacings set forth below:

| SAPO-41 | | |
|---|---|---|
| $2\theta$ | d(Å) | Relative Intensity |
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.44 | w–m |

NZMS ALKYLATION CATALYSTS

The specific NZMSs employed in the instant invention are characterized in their calcined form by an adsorption of isobutane of at least 2 percent by weight, preferably at least 4 percent by weight, at a partial pressure of 500 torr and a partial temperature of 20° C. and are also characterized in their calcined form by and adsorption of triethylamine of less than 5 percent by weight, preferably less than 3 percent by weight, at a partial pressure of 2.6 torr and a temperature of 22° C. NZMSs characterized by the above described adsorption of isobutane and triethylamine include, but are not limited to, ELAPSO-11, ELAPSO-31, ELAPSO-41, SAPO-11, SAPO-31, SAPO-41, CoAPSO-11, CoAPSO-31, CoAPSO-41, FeAPSO-11, FeAPSO-31, FeAPSO-41, MgAPSO-11, MgAPSO-31, MgAPSO-41, MnAPSO-11, MnAPSO-31, MNAPSO-41, TiAPSO-11, TiAPSO-31, TiAPSO-41, ZnAPSO-11, ZnAPSO-31, ZnAPSO-41, CoMgAPSO-11, CoMgAPSO-31, CoMgAPSO-41, CoMnMgAPSO-11, CoMnMgAPSO-31, CoMgMnAPSO-41, MeAPO-11, MeAPO-31, MeAPO-41, TiAPO-11, TiAPO-31, TiAPO-41, FeAPO-11, FeAPO-31, FeAPO-41, FCAPO-11, FCAPO-31, FCAPO-41 and mixtures thereof.

The above characterization of the NZMSs employed in the instant invention relates to an adsorption characterization that is carried out on a NZMS which has been subjected to a post synthesis treatment, e.g., calcination or chemical treatment, to remove a substantial portion of the template "R" which is present as a result of synthesis. Although a particular NZMS is characterized herein by reference to its adsorption of isobutane and triethylamine as being to the adsorption characteristics of the NZMS in its calcined form, the instant invention necessarily includes the use of a non calcined or modified NZMSs which may be characterized by such adsorption in or modified the calcined form, since upon use of such a non-calcined NZMS in the instant process at effective process conditions the NZMS may be calcined or hydrothermally treated in situ so as to have the characteristic adsorption of isobutane or triethylamine. Thus, the NZMS may be rendered in situ to a form characterized by the aforementioned adsorption characteristics. For example, an as-synthesized MgAPO-11 or MgAPSO-11 may not be characterized by the aforementioned adsorption of isobutane and triethylamine due to the presence of template "R" which is present as a result of synthesis, although the calcined form of MgAPO-11 and MgAPSO-11 will be characterized by the aforementioned adsorption of isobutane and triethylamine. Thus, reference to a NZMS having a particular adsorption characteristic in its calcined form is not intended to exclude the use of the NZMS in its as-synthesized form which upon in situ calcination, in-situ hydrothermal treatment and/or other treatment, e.g., chemical treatment with one or more compounds capable of removing organic template, would have such adsorption characteristics.

The NZMSs of the instant invention may be employed with traditional alkylation catalysts and optionally, a zeolitic aluminosilicate alkylation catalyst may be employed in conjunction with a NZMS containing alkylation catalyst of this invention.

FORMULATION OF NZMS ALKYLATION CATALYSTS

The alkylation catalysts of the instant invention comprise an effective amount of at least one NZMS, as above characterized. The relative amount of the NZMS component will depend at least in part, on the selected feedstock and on the desired product distribution of xylene and/or other bi-substituted aromatics to be obtained therefrom, but in all instances an effective amount of at least one NZMS is employed.

The alkylation catalysts of this invention are typically employed with an inorganic oxide matrix components such as heretofore employed in the formulation of catalysts including: amorphous inorganic oxides, e.g., clays, silicas, aluminas, and the like and mixtures thereof.

ALKYLATION PROCESSES

The instant alkylation process may be carried out at effective alkylation conditions as heretofore employed in the art for alkylation processes. Excessively high pressures, will be generally undesirable, though fully operative, because of the great strength of reaction vessel walls required at high pressure, making the equipment unnecessarily expensive and requiring expensive compression stages. In general, temperature and WHSV will be coordinated to provide a desired severity which will provide an adequate degree of alkylation of the starting aromatic compound without excessive losses to by-products. Temeratures in the lower part of the temperature range will normally call for low space velocities. The instant process may be carried out in the presence of added hydrogen, although such is not generally preferred.

The instant alkylation process is carried out at effective process conditions of temperature pressure, molar ratios of reactants, etc. The effective temperature is generally between about 50° C. and about 600° C., preferably between about 200° C. and about 500° C. and is more preferably between about 300° C. and about 450° C. The effective pressure is generally between 0 psig and about 1000 psig and is preferably between greater than 0 psig and about 200 psig. The WHSV (Weight Hourly Space Velocity) will generally be between about 0.1 and about 100 and is typically between about 1 and about 10, and preferably about 5 to 10. The molar ratio of the alkylating agent, e.g., an aliphatic alcohol such as methanol, is generally between about 1:50 to 50:1 and is preferably between about 1:10 to 1:1 The alkylating agent may be most any alkylating agent effective in the alkylation of mono-substituted aromatics, e.g., toluene, and may be of the formula "RX" where "R" may be an alkyl or substituted alkyl group having from 1 to 30 carbon atoms and "X" may be halide (preferably chloride or bromide), hydroxyl, carbonate, carbonyl, alkoxyl and alkyl sulfide where the alkyl group contains 1 to 30 carbon atoms. Representative of alkylating agents employable herein include methanol, ethanol, methylchloride, methylbromide, dimethylether, ethylmethylether, methylcarbonate and dimethylsulfide. Light olefins ($C_1$ to $C_4$) may also be employed as alkylating agents.

The alkylation process may be carried out in a batch, semi-continuous or continuous manner using a fixed or moving bed catalgst. In one embodiment a fluidized catalyst bed is employed where an aromatic compound and an alkylating agent are contacted concurrently through a moving bed of catalyst. The catalyst may be regenerated after use by regeneration in an oxygen containing atmosphere whereby coke deposited on the catalyst is burned.

According to this invention, it is possible to selectively alkylate aromatics in the para-position, e.g., the methylation of toluene to para-xylene.

Several compositions were prepared for use in the following examples and were prepared as follows:

(a) AlPO$_4$-11 was prepared by blending 274.8 grams of CATAPAL TM SB alumina in 1192 grams of water. This mixture was added to 461.2 grams of 85 wt. % orthophosphoric acid ($H_3PO_4$). Di-isopropyl amine (20.2 grams) was added to the above mixture and the resulting mixture blended until a homogeneous mixture was observed. This mixture was digested at 200° C. for 48 hours. The solid product was washed with water, dried in air and calcined in air to remove the template.

(b) AlPO$_4$-31 was prepared by mixing 715.2 grams of water, 164.8 grams of CATAPAL TM SB alumina, 276 grams of 85 wt. % $H_3PO_4$ and 121.4 grams of dipropylamine. The mixture was blended to form a homogeneous mixture and then digested at 200° C. for 48 hours. The product was then water washed, dried in air and calcined in air to remove the template.

(c) SAPO-5 was prepared by mixing 13.8 grams of CATAPAL TM SB alumina with 23.1 grams of 85 wt. % $H_3PO_4$ dissolved in 28.7 grams of water. CABOSIL TM (3.88 grams) was added to the aforementioned mixture in 58.8 grams of tripropylamine. The mixture was blended to form a homogeneous mixture and then digested at 200° C. for 24 hours. The product was then water washed, dried in air and calcined in air to remove the template.

(d) SAPO-11 was prepared by blending 409 grams of aluminum isopropoxide with 231 grams of 85 wt. % orthophosphoric acid in 750 grams of water LUDOX TM LS silica in 50 grams of water was added to the aforementioned mixture. The resulting mixture was blended to form a homogeneous mixture and then digested at 200° C. for 48 hours. The product was then water washed, dried in air and calcined in air to remove the template.

(e) SAPO-31 was prepared by blending 81.7 grams of aluminum isopropoxide, 46.1 grams of 85 wt. % orthophosphoric acid, 24.0 grams of LUDOX TM LS silica gel, 20.2 grams of di-n-propylamine and 161.8 grams of water. The resulting mixture was blended to form a homogeneous mixture and then 5.6 grams of AlPO$_4$-31 seed crystals added. The resulting mixture was digested for 3.8 days at 200° C. The solid product was water washed , dried in air and calcined in air at 550° C. for 2 hours.

(f) SAPO-40 was prepared by blending 22.1 grams of CATAPAL TM alumina with 36.9 grams of 85 wt. % phosphoric acid dissolved in 35.72 grams of water. Tetrapropyl ammonium hydroxide (162.8 grams of a 40 wt. % solution in water containing 0.12 grams of sodium hydroxide) was added to the first mixture. The resulting mixture was blended to form a homogeneous mixture and then digested for 24 hours at 225° C. The solid product was water washed, dried in air and calcined in air to remove template. Analysis by x-ray of the SAPO-40 product indicated a SAPO-5 impurity phase comprising at least 25 wt. % of the solid product.

(g) SAPO-41 was prepared by blending 27.6 grams of CATAPAL TM alumina with 46.1 grams of 85 wt. % orthophosphoric acid in 109.7 grams of water. This mixture was blended with a slurry of 5.2 grams CABO-SIL TM silica, 129.9 grams tetrabutylammonium hydroxide and 80 grams of water. The resulting mixture was blended to form a homogeneous mixture and digested for 24 hours. The solid product was water washed, dried in air and calcined in air to remove template. X-ray analysis of the product indicated a tridimite impurity phase comprising 40 wt. % of the solid product.

EXAMPLES

The following examples were carried out to demonstrate the invention and are not intended to be limiting thereof.

EXAMPLES 1–9

Catalysts containing $AlPO_4$-11 $AlPO_4$-31, SAPO-5, SAPO 11, SAPO-31, SAPO-40, and SAPO-41 were evaluated as alkylation catalysts. The $AlPO_4$s and SAPOs were prepared according to U.S. Pat. Nos. 4,310,440 and 4,440,871, respectively, as above described. A comparative catalyst was prepared using LZ-105. LZ-105 was prepared according to U.S. Pat. No. 4,257,885 and acid washed prior to use with 1 normal HCl acid to generate Bronsted acid sites.

The evaluation of a given catalyst was carried out using a stainless steel micro reactor having a ¼" ID. Each catalyst is evaluated as the powder by introducing the powder into the reactor. The feedstock was fed to the reactor by a syringe pump and the reactor temperature is maintained by heating the reactor in a fluidized sandbath. The sandbath temperature is controlled by a thermocouple temperature indicator located in the catalyst bed. Prior to operation the reactor is pressurized to 100 psig with a nitrogen purge. The syringe pump is filled with feed and the reactor and catalyst preheated to 800° F. The feed was then introduced into the reactor and liquid sample products collected at 0.5 hour intervals for from 2 to up to 5 hours. The evaluation conditions were as follows:

Feed: Toluene/Methanol in a molar ratio of 2/1
  Feed Rate: 8 cubic centimeters per hour
  Pressure: 100 psig.
  Temperature: 800° F.

Gas products were not collected. Liquid products were analyzed by vapor phase chromatography.

Table I sets forth the results of the evaluation of the above noted catalysts.

Examples 1 and 2 report the comparative results of the use of $AlPO_4$-11 and $AlPO_4$-31. $AlPO_4$-11 and $AlPO_4$-31 are not zeolites, i.e., are not aluminosilicates, and do not contain at least three framework elements as do the claimed non zeolitic molecular sieves (NZMSs). As shown in Table I, although $AlPO_4$-11 and $AlPO_4$-31 are both not zeolites and have adsorption characteristics similar to the instant NZMSs, such do not contain at least 3 framework elements as tetrahedral oxides, e.g., $TiO_2$, and do not provide for the effective alkylation of toluene to xylenes. In example 3 (SAPO-5) and in example 6 (a mixture of SAPO-40 and SAPO-5), the effect of at least a 25 weight percent SAPO-5 (not characterized by the adsorption characteristics of the NZMSs of this invention) is shown. In examples 4, 5, 6 and 7 the NZMSs denominated SAPO-11, SAPO-31 and SAPO-41 (NZMSs characterized by the adsorption criteria of the instant invention and containing $SiO_2$, $AlO_2$ and $PO_2$ tetrahedral units i.e., NZMSs according to this invention) were evaluated. Examples 4, 5 and 7 demonstrate catalysts according to this invention that provide high selectivity to the desired para-xylene product. SAPO-11, SAPO-31, SAPO-40 and SAPO-41 each gave a para-xylene selectivity greater than 25%. This amount is in excess of the amount present as a result of simple thermodynamic equilibrium.

The NZMSs having the characteristic composition and adsorption criteria of those employable in the instant process demonstrate a high selectivity to xylene products, high selectivity to para-xylene in the total xylene products.

TABLE I

| | 1[8] | 2[8] | 3 | 4 | 5 | 6 | 7 | 8[8] | 9 |
|---|---|---|---|---|---|---|---|---|---|
| Molecular Sieve Component[1] | $AlPO_4$-11 | $AlPO_4$-31 | SAPO-5 | SAPO-11 | SAPO-31 | SAPO-40 | SAPO-41 | LZ-105 | — |
| Time on stream (minutes): | 120 | 120 | 105 | 120 | 125 | 90 | 90 | 120 | — |
| AROMATIC PRODUCTS (Wt. %): | | | | | | | | | |
| Benzene | 0.03 | 0.03 | 6.07 | 0.19 | 0.14 | 0.02 | 0.06 | 11.10 | — |
| Toluene | 99.19 | 97.47 | 63.21 | 62.95 | 73.26 | 96.08 | 90.01 | 52.19 | — |
| Ethyl Benzene | 0.0 | 0.01 | 0.26 | 0.02 | 0.0 | 0.0 | 0.2 | 0.71 | — |
| Xylenes (Total) | 0.76 | 2.17 | 20.81 | 26.88 | 16.98 | 3.24 | 7.23 | 26.56 | — |
| para-xylene | 0.28 | 0.95 | 5.03 | 10.40 | 6.50 | 0.98 | 2.27 | 6.29 | — |
| meta-xylene | 0.18 | 0.42 | 10.49 | 11.34 | 5.48 | 0.74 | 2.59 | 14.13 | — |
| ortho-xylene | 0.30 | 0.80 | 5.29 | 5.14 | 5.00 | 1.52 | 2.37 | 6.14 | — |
| $C_9+$ Aromatics | 0.03 | 0.32 | 9.63 | 9.76 | 9.60 | 0.58 | 2.67 | 9.43 | — |
| Toluene Conversion[2]: | 0.7 | 2.16 | 34.0 | 33.0 | 23.2 | 3.3 | 8.5 | 45.6 | — |
| % Selectivity to Xylenes (Total):[3] | —[6] | —[6] | 61.2 | 81.5 | 73.2 | 97.3 | 85.5 | 58.2 | — |
| % Para-Xylene Selectivity:[4] | —[6] | —[6] | 14.8 | 31.5 | 28.0 | 29.4 | 26.8 | 13.8 | — |
| % Para-Xylene in Total Xylenes:[5] | —[6] | —[6] | 24.2 | 38.7 | 38.3 | 30.2 | 31.4 | 23.7 | 23.4[7,8] |

[1]Molecular sieve component in the alkylation catalyst at 100 weight percent.
[2]Toluene Conversion = (Weight percent toluene in Feed) − (Weight Percent Toluene in Product)
[3]Xylene Selectivity = $\frac{\text{(Weight Percent Xylene in Product)}}{\text{(Toluene Conversion)}} \times 100$
[4]Para-xylene Selectivity = $\frac{\text{(Weight Percent Para-Xylene in Product)}}{\text{Toluene Conversion}} \times 100$
[5]% Para-Xylene in Total Xylene = $\frac{\text{Weight Percent Para-Xylene in Product}}{\text{(Weight Percent Xylenes in Product)}} \times 100$
[6]Conversion is too small to quantify Xylenes.
[7]Weight Percent para-xylene in a xylene mixture as a result of thermodynamic equilibrium.
[8]Comparative examples.

We claim:

1. A process for the selective para-alkylation of mon-substituted aromatic compounds comprising reacting the aromatic compound with an effective amount of an alkylating agent at effective alkylating conditions in the presence of a catalyst comprising an effective amount of at least one NZMS containing at least three framework elements as tetrahedral oxides and characterized in its active catalytic form by an adsorption of isobutane of at least 2 percent by weight at a partial pressure of 500 torr and a temperature of 20° C. and also characterized in its active catalytic form by an absorption of triethylamine less than 5 percent by weight at a pressure of 2.6 torr and a temperature of 22° C.

2. The process of claim 1 wherein said NZMS is characterized in its calcined form by an adsorption of isobutane of at least 4 percent by weight at a pressure of 500 torr and a temperature of 20° C.

3. The process of claim 1 wherein said NZMS is further characterized in its calcined form by an adsorption of triethylamine less than 3 percent by weight at a pressure of 2.6 torr and a temperature of 22° C.

4. The process of claim 1 or claim 2 wherein said effective process conditions include a temperature between about 50° C. and about 500° C.

5. The process of claim 4 wherein said effective process conditions include a temperature between about 30° C. and about 450° C.

6. The process of claim 1 wherein said catalyst comprises an inorganic oxide component in an amount between about 5 and about 95 percent by weight, based on the total weight of said catalyst.

7. The process of claim 1 or claim 2 wherein said NZMS has at least part of its cations as H+ or hydrogen forming species.

8. The process of claim 7 wherein said hydrogen forming species is $NH_4^+$ or $H^+$.

9. The process of claim 1 or claim 2 wherein the process is carried out at an effective temperature between about 100° C. and about 500° C., effective pressure between zero psig and about 1000 psig, a WHSV of between about 0.1 and about 100 and a molar ratio of alkylating agent to mono-substituted aromatic compounds of between 1:50 and 50:1.

10. The process of 6 wherein said inorganic oxide matrix component is selected from the group consisting of clays, silicas, aluminas, and mixtures thereof.

11. The process of claim 1 or claim 2 or claim 3 wherein said NZMS is selected from the group consisting of CoAPSOs, FeAPSOs, MgAPSOs, MnAPSOs, TiAPSOs, ZnAPSOs, CoMgAPSOs, CoMnMgAPSOs, MeAPOs, TiAPOs, FeAPOs, FCAPOs and mixture thereof.

12. The process of claim 1 or claim 2 wherein said NZMS is selected from the group consisting of CoAPSOs, FeAPSOs, MgAPSOs, MnAPSOs, TiAPSOs, ZnAPSOs, CoMgAPSOs, CoMnMgAPSOs and mixtures thereof.

13. The process of claim 1 or claim 2 or claim 3 wherein said NZMS is selected from the group consisting of ELAPSO-11, ELAPSO-31, ELAPSO-41, and mixtures thereof.

14. The process of claim 13 wherein said NZMS is selected from the group consisting of SAPO-11, SAPO-31, SAPO-41, CoAPSO-11, CoAPSO-31, CoAPSO-41, FeAPSO-11, FeAPS-31, FeAPSO-41, MgAPSO-11, MgAPSO-31, MgAPSO041, MnAPSO-11, MnAPSO-31, MnAPSO-41, TiAPSO-11, TiAPSO-31, TiAPSO-41, ZnAPSO-11, ZnAPSO-31, ZnAPSO-41, CoMgAPSO-11, CoMgAPSO-31, CoMgAPSO-41, CoMnMgAPSO-11, CoMnMgAPSO-31, CoMnMgAPSO-41 and mixtures thereof.

15. The process of claim 1 or claim 2 or claim 3 wherein said NZMS is selected from the group consisting of MeAPO011, MeAPO-31, MeAPO-41, TiAPO-11, TiAPO-31, TiAPO-41, FeAPO-11, FeAPO-31, FeAPO-41, FCAPO-11, FCAPO-31, FCAPO-41 and mixtures thereof.

16. The process of claim 15 wherein "Me" is selected from the group consisting of cobalt magnesium, manganese, zinc and mixtures thereof.

17. The process of claim 15 wherein "Me" is selected from the group consisting of magnesium, manganese and mixtures thereof.

18. The process according to claim 1 wherein said mono-substituted aromatic is at least one selected from the group consisting of mono-alkylbenzenes, chlorobenzene, fluorobenzene, bromobenzene and said alkylating agent is at least one selected from the group consisting of olefins and compounds of the formula "RX" wherein "R" is an alkyl or substitued alkyl containing from 1 to 30 carbon atoms and "X" is halide, hydroxyl carbonate, carbonyl, alkoxyl, alkylsulfide.

19. In a process for the selective production of paraxylene by the reaction of toluene with a methylating agent under effective methylation conditions in the presence of a methylation catalyst, the improvement which comprises reacting toluene and said methylating agent in the presence of a methylation catalyst containing at least one NZMS containing at least three framework elements as tetrahedral oxides and characterized in its active catalytic form by an adsorption of isobutane of at least 2 percent by weight at a partial pressure of 500 torr and a temperature of 20° C. and also characterized in its active catalytic form by an adsorption of triethylamine less than 5 percent by weight at a pressure of 2.6 torr and a temperature of 22° C.

* * * * *